US008026070B2

(12) United States Patent
An et al.

(10) Patent No.: US 8,026,070 B2
(45) Date of Patent: Sep. 27, 2011

(54) DIFFERENTIAL DETECTION OF MULTIMERIC AND MONOMERIC FORMS OF MULTIMER-FORMING POLYPEPTIDES

(75) Inventors: Seong Soo Alexander An, Ithaca, NY (US); Kun Taek Lim, Seoul (KR); Hyun Jung Oh, Seoul (KR)

(73) Assignee: Peoplebio, Inc., Seoul (KR)

( * ) Notice: Subject to any disclaimer, the term of this patent is extended or adjusted under 35 U.S.C. 154(b) by 804 days.

(21) Appl. No.: 11/816,261

(22) PCT Filed: Nov. 25, 2005

(86) PCT No.: PCT/KR2005/004001

§ 371 (c)(1), (2), (4) Date: May 5, 2008

(87) PCT Pub. No.: WO2006/088281

PCT Pub. Date: Aug. 24, 2006

(65) Prior Publication Data

US 2010/0009388 A1 Jan. 14, 2010

(30) Foreign Application Priority Data

Feb. 19, 2005 (KR) ........................ 10-2005-0013877
Mar. 11, 2005 (WO) ................ PCT/KR2005/000733

(51) Int. Cl.
*G01N 33/53* (2006.01)

(52) U.S. Cl. ........................... 435/7.1; 436/518; 435/7.2

(58) Field of Classification Search ........................ None
See application file for complete search history.

(56) References Cited

U.S. PATENT DOCUMENTS

| | | | | |
|---|---|---|---|---|
| 6,750,025 | B1 | 6/2004 | Hammond et al. | |
| 6,780,979 | B1 * | 8/2004 | Deslys | 530/412 |
| 6,846,640 | B2 | 1/2005 | Peach et al. | |
| 2003/0082827 | A1 | 5/2003 | Craig et al. | |
| 2007/0077603 | A1 * | 4/2007 | Heeb et al. | 435/7.5 |

OTHER PUBLICATIONS

Foster et al. (Veterinary Record 1996, vol. 139, p. 512-515.*
Serbec et al. (J Biol Chem 2004, vol. 279, p. 3694-3698).*
Šerbec et al., "Monoclonal Antibody against a Peptide of Human Prion Protein Discriminates between Creutzfeldt-Jacob's Disease-affected and Normal Brain Tissue," The Journal of Biological Chemistry, Oct. 29, 2003, vol. 279, No. 5, Issue of Jan. 30, pp. 3694-3698, 2004 (DOI 10.1074/jbc.M310868200).
Jiri Safar, et al., "Eight prion strains have PrPSc molecules with different conformations", Nature Medicine, Oct. 1998, pp. 1157-1165, vol. 4, No. 10.

* cited by examiner

*Primary Examiner* — Jacob Cheu
(74) *Attorney, Agent, or Firm* — The Nath Law Group; Joshua B. Goldberg; Mihsuhn Koh

(57) ABSTRACT

A method for differentially detecting a multimeric form from a monomeric form of a multimer-forming polypeptide in a biosample includes (a) contacting the biosample to a capturing antibody recognizing an epitope on the multimer-forming polypeptide to capture the monomeric form, multimeric form or monomeric and multimeric forms; (b) contacting the monomeric form, multimeric form or monomeric and multimeric forms captured to a detecting antibody recognizing an epitope identical to or overlapped with the epitope of step (a); and (c) detecting the formation of a multimeric form-detection antibody complex.

17 Claims, 14 Drawing Sheets

Agglutination

DIFFERENTIAL DETECTION OF MULTIMERIC AND MONOMERIC FORMS OF MULTIMER-FORMING POLYPEPTIDES

CROSS-REFERENCES TO RELATED APPLICATIONS

This is a US National Stage of International Application PCT/KR2005/000733 filed Mar. 11, 2005, with the Republic of Korea Receiving Office under the PCT; and the benefit of priority is further claimed to Republic of Korea patent application 10-2005-0013877 filed Feb. 19, 2005, with the Korean Intellectual Property Office, both applications being incorporated herein by reference.

BACKGROUND

1. Field of the Invention

The present invention relates to methods for differentially detecting a multimeric form from a monomeric form of a multimer-forming polypeptide and immunoassay kits therefor.

2. Description of the Related Art

A multimerization of polypeptides constituting proteins has been generally known to be required for the function of proteins. However, the multimeric forms often cause diseases or disorders in some proteins. In particular, a protein exists as a monomer in normal conditions and is converted to a multimer (or aggregate form) in abnormal conditions (e.g., by the conversion to a misfolding form).

It has been well established that proteins that are misfolded and ultimately aggregated (or accumulated), i.e., that are not in their functionally relevant conformation are devoid of normal biological activity. The failure to fold correctly, or to remain correctly folded, gives rise to many different types of biological malfunctions and hence, to many different forms of diseases (Massimo Stefani, et al., *J. Mol. Med.* 81:678-699 (2003); and Radford S E, et al., *Cell.* 97:291-298(1999)). Many diseases ultimately result from the presence in a living system of protein molecules with structures that are incorrect, i.e., that differ from those in normally functioning organisms.

For instance, the diseases or disorders associated with abnormal aggregation or misfolding of proteins include Alzheimer's disease, Creutzfeldt-Jakob disease, Spongiform encephalopathies, Parkinson's disease, Huntington's disease, Amyotrophic lateral sclerosis, Serpin deficiency, emphysema, cirrhosis, Type II Diabetes, primary systemic amyloidosis, secondary systemic amyloidosis Fronto-temporal dementias, senile systemic amyloidosis, familial amyloid polyneuropathy, hereditary cerebral amyloid angiopathy and haemodialysis-related amyloidosis.

Early diagnosis of the aggregation-associated diseases has been intensively studied. However, there has not been suggested any process and approach to differentially detect multimeric (aggregating) forms from their monomeric (normal) forms.

Sporadic, variant, iatrogenic, and familial Creutzfeldt-Jakob diseases, kuru, Familial Fatal insomnia, and Gerstmann-Straussler-Scheinker syndrome in humans, scrapie in sheep and goats, feline spongiform encephalopathy in cat, mink spongiform encephalopathy, Chronic Wasting disease in deer, elk, and moose, and bovine spongiform encephalopathy in cattle are the fatal neurodegenerative diseases, due to transmissible spongiform encephalopathies (TSE) (Prusiner S. B. *Proc. Natl. Acad. Sci. USA* 95:13363-13383(1998); and Hope J. *Curr. Opin. Genet. Dev.* 10, 568-57(2000)). Abnormal isoform or the scrapie form of prion protein ($PrP^{Sc}$) has been strongly suggested to the main culprit of TSE (Caughey B. *Trends Biochem. Sci.* 26:235-42(2001)).

The normal form of the prion protein ($PrP^{C}$), contains both an a-helical and a flexibly disordered portion and exists as a monomeric form (Zahn, R., et al., *Proc. Natl. Acad. Sci. USA* 97:145-150(2000)), where the scrapie form ($PrP^{Sc}$) has highly β-sheet conformation and exists as a multimeric (aggregating) or at least dimer forms (Caughey, B., et al., *J. Biol. Chem.* 273:32230-35(1998)). The conformational change from α-helical to β-sheet conformations is the central event of the disease that seems to be responsible for its neuropathology.

While $PrP^{C}$ is protease sensitive ($PrP^{sen}$), $PrP^{Sc}$ is partially resistant to proteolysis ($PrP^{res}$) and prone to form high-molecular-weight aggregates (Bolton D. C. *Lancet,* 358:164-5 (2001)). This latter feature makes it difficult to analyze the conformational transition that leads to the formation of $PrP^{res}$ or to characterize it.

The method of proteinase K (PK) digestion has been used to discriminate the resistance of its various forms of PrP (scrapie form) by digesting the cellular form, leaving only the scrapie form to be detected in ELISA. However, the PK digestion method is being questioned. PrP conformation, concentration, tissue antibodies, digestion time and buffers could influence the PK sensitivity, which significantly reduces the reliability of the PK digestion method.

Therefore, there remains a need to develop a novel approach for differentially detecting multimeric form (e.g., scrapie form of PrP) from their monomeric forms (e.g., cellular form of PrP) with much higher reliability and convenience.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

Under such circumstances, the present inventors have made intensive research to develop a novel method for differentially detecting multimeric (aggregating) forms from monomeric forms of multimer-forming polypeptides, and as a result, developed a novel immunoassay approach using a unique set of capturing and detecting antibodies.

Accordingly, it is an object of this invention to provide a method for differentially detecting a multimeric form from a monomeric form of a multimer-forming polypeptide in a biosample.

It is another object of this invention to provide a kit for differentially detecting a multimeric form from a monomeric form of a multimer-forming polypeptide in a biosample.

It is still another object of this invention to provide a method for differentially detecting a multimeric form from a monomeric form of a multimer-forming polypeptide based on agglutination.

Other objects and advantages of the present invention will become apparent from the detailed description to follow and together with the appended claims and drawings.

INCORPORATION OF SEQUENCE LISTING

Figure 1:
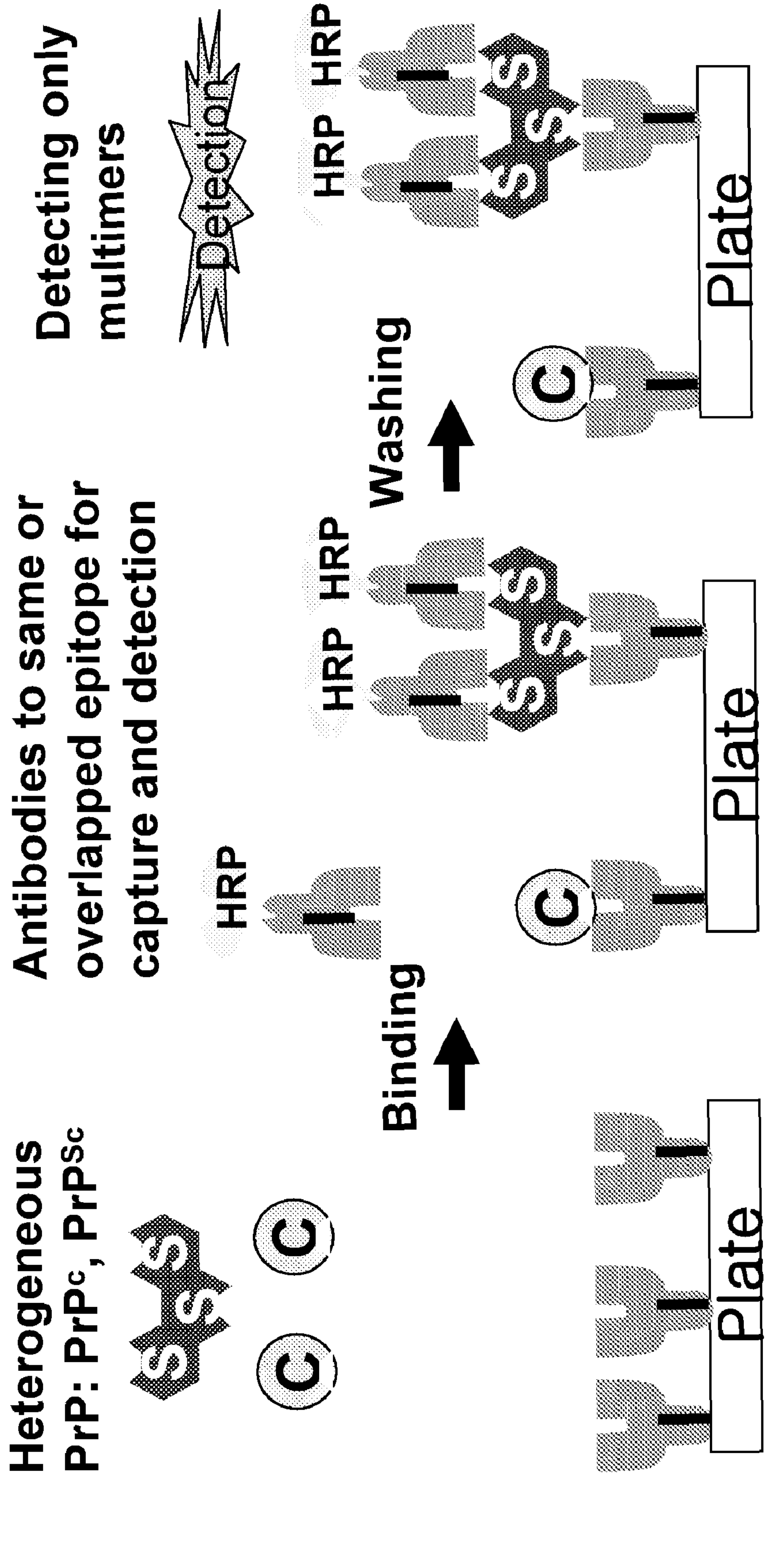
FIG. 1 schematically represents the processes of a specific embodiment of this invention.

The entire contents of the accompanying Sequence Listing, as filed herewith in computer-readable format, are incorporated herein by reference.

DETAILED DESCRIPTION

In one aspect of this invention, there is provided a method for differentially detecting a multimeric form from a monomeric form of a multimer-forming polypeptide in a biosample, which comprises the steps of: (a) contacting the biosample to a capturing antibody recognizing an epitope on the multimer-forming polypeptide to capture the monomeric form, multimeric form or monomeric and multimeric forms; (b) contacting the monomeric form, multimeric form or monomeric and multimeric forms captured to a detecting antibody recognizing an epitope identical to or overlapped with the epitope of step (a); and (c) detecting the formation of a multimeric form-detection antibody complex.

In another aspect of this invention, there is provided a kit for differentially detecting a multimeric form from a monomeric form of a multimer-forming polypeptide in a biosample, which comprises (a) a capturing antibody recognizing an epitope on the multimer-forming polypeptide; and (b) a detecting antibody, which comprises (a) a capturing antibody recognizing an epitope on the multimer-forming polypeptide; and (b) a detecting antibody recognizing an epitope identical to or overlapped with the epitope recognized by the capturing antibody.

The present invention is directed to a method for differentially detecting a multimeric form from a monomeric form of a multimer-forming polypeptide in a biosample by immunoassay involving antigen-antibody reactions. The present method is named "Multimer Detection Method" (abbreviated as MDS).

The term "multimer-forming polypeptide" used herein refers to a polypeptide capable of forming an aggregation form, particularly, following conformational change, causing a wide variety of diseases such as Alzheimer's disease, Creutzfeldt-Jakob disease, Spongiform encephalopathies, Parkinson's disease, Huntington's disease, Amyotrophic lateral sclerosis, Serpin deficiency, emphysema, cirrhosis, Type II diabetes, primary systemic amyloidosis, secondary systemic amyloidosis Fronto-temporal dementias, senile systemic amyloidosis, familial amyloid polyneuropathy, hereditary cerebral amyloid angiopathy and haemodialysis-related amyloidosis. Therefore, the term "multimer-forming polypeptide" will be interchangeably used with the term "aggregate-forming polypeptide".

Generally, a monomeric form (i.e., non-aggregation form) of the multimer-forming polypeptide is normal and a multimeric form (i.e., aggregation form) is infective to cause diseases, in particular, neurodegenerative diseases such as Alzheimer's disease and Creutzfeldt-Jakob disease.

According to a preferred embodiment, the multimer-forming polypeptide includes Aβ peptide and tau protein related to Alzheimer's disease, prion related to Creutzfeldt-Jakob disease and Spongiform encephalopathies, α-synuclein related to Parkinson's disease Ig light chains related to primary systemic amyloidosis, serum amyloid A related to secondary systemic amyloidosis, tau related to Fronto-temporal dementias, transthyretin related to senile systemic amyloidosis, transthyretin related to familial amyloid polyneuropathy, cystatin C related to hereditary cerebral amyloid angiopathy, $\beta_2$-microglobulin related to haemodialysis-related amyloidosis, huntingtin related to Huntington's disease, superoxide dismutase related to Amyotrophic lateral sclerosis, serpin related to Serpin deficiency, emphysema, and cirrhosis, and amylin related to Type II Diabetes. More preferably, the multimer-forming polypeptide is the prion protein causing Creutzfeldt-Jakob disease and Spongiform encephalopathies. When the present method is applied to the prion protein (PrP), the monomeric form is $PrP^{c}$ (cellular or normal form of prion) and the multimeric form is $PrP^{Sc}$ (scrapie or infectious form of prion).

The present method uses two types of antibodies, i.e., capturing antibody and detecting antibody. As used herein, the term "capturing antibody" means an antibody capable of binding to the multimer-forming polypeptide of interest in biosamples. The term "detecting antibody" means an antibody capable of binding to the multimer-forming polypeptide captured by the capturing antibody. By "antibody" is meant an immunoglobulin protein which is capable of binding an antigen. Antibody as used herein is meant to include the entire antibody as well as any antibody fragments (e.g., F(ab')2, Fab', Fab, Fv) capable of binding the epitope, antigen or antigenic fragment of interest.

The striking feature of this invention is to use a set of capturing antibody and detecting antibody specifically recognizing an epitope on the multimer-forming polypeptide in which the epitopes specifically recognized by the capturing antibody and detecting antibody are identical to or overlapped, with each other.

The term "overlapped with" used herein with referring to epitopes to capturing and detecting antibodies encompasses epitopes having completely or partially overlapped amino acid sequences. For example, the epitopes to 3O8 and 3F4 antibodies have amino acid sequences spanning amino acid 106-126 and 109-112, respectively, of a human prion sequence, as found in Examples. Such epitopes can be described as completely overlapped epitopes.

According to a specific and preferable embodiment, the epitope has an amino acid sequence spanning amino acid 109-112, 106-126, 132-147, 135-140, 146-151, 144-153, 143-151, 129-149 or 112-125, more preferably, amino acid 109-112, 106-126, 132-147, 135-140, 146-151, 143-151, and most preferably, amino acid 109-112, 106-126, 132-147 or 135-140, if indicated with referring to a human prion sequence. The most preferable antibody reactive with $PrP_{109-112}$ is 3F4 as described in U.S. Pat. No. 4,806,627 (commercially available from Sigma). The most preferable antibody reactive with $PrP_{106-126}$ is 3O8 as described in Hisako Furukawa, et al., *J. Biol. Chem.,* 279: 23661-23667(2004)

According to a preferred embodiment, the epitope specifically recognized by the capturing antibody is not repeated in the multimer-forming polypeptide. Preferably, the epitope specifically recognized by the detecting antibody is not repeated in the multimer-forming polypeptide. According to the present method, the multimer-forming polypeptide bound to the capturing antibody cannot be further combined with the detecting antibody due to the absence of additional epitopes recognized by the detecting antibody.

The epitopes for preparing the capturing and/or detecting antibodies should be firstly selected to be found only once on the multimer-forming polypeptide. For example, a gly-repeated sequence is present at several positions on prion; therefore, it is not suitable as epitopes in this invention. Preferably, the epitope is selected at amino acid 95-180 if expressed with referring to a human prion sequence described in SEQ ID NO:1. More preferably, the epitope is selected at amino acid 100-160 and most preferably, 109-153.

According to a specific and preferable embodiment, the epitope has an amino acid sequence spanning amino acid 109-112, 106-126, 132-147, 135-140, 146-151, 144-153, 143-151, 129-149 or 112-125, more preferably, amino acid 109-112, 106-126, 132-147, 135-140, 146-151, 143-151, and most preferably, amino acid 109-112, 106-126, 132-147 or 135-140, if indicated with referring to a human prion sequence. The most preferable antibody reactive with $PrP_{109-112}$ is 3F4 as described in U.S. Pat. No. 4,806,627 (commercially available from Sigma). The most preferable antibody reactive with $PrP_{106-126}$ is 3O8 as described in Hisako Furukawa, et al., *J. Biol. Chem.,* 279: 23661-23667(2004) (commercially available from Cayman Chemical). As an antibody reactive with $PrP_{132-147}$, MA1-750 described in Yoichi Matsunaga et al., Proteins, 44:110(2001) (commercially available from Affinity BioReagents, Inc) is the most preferable. T2 as described in Hiroko Hayashi, et al., *J. Vet. Med. Sci.,* 66(6):515(2004) is the most preferable antibody reactive with $PrP_{135-140}$. Most preferably, antibodies specifically recognizing $PrP_{146-151}$, $PrP_{144-153}$, $PrP_{143-151}$, $PrP_{129-149}$, and $PrP_{112-125}$, are 1F5, SAF antibody (commercially available from Cayman Chemical), 6H4 (purchasable from Prionics AG), 1E5/G6 (purchasable from Novus Biologicals) and 7B6/D2 (purchasable from Novus Biologicals), respectively.

Where the present method is applied to bovine biosamples, antibodies recognizing the epitopes of amino acids 135-140 (amino acids 145-150 of SEQ ID NO:2 if indicated with referring to a bovine prion sequence) (e.g., T2 antibody) or 132-147 (amino acids 142-157 of SEQ ID NO:2 if indicated with referring to a bovine prion sequence) (e.g., MA1-750 antibody) are the most preferable. For example, a series of antibody sets of MA1-750/MA1-750, MA1-750/T2, T2/T2 or T2/MA1-750 for the capturing and detecting antibodies is very useful in the present method for bovine samples.

Where the present method is used to analysis biosamples (in particular, plasma) from human, it is preferable to use antibodies to the epitopes of amino acids 109-112 (e.g., 3F4 antibody), 106-126 (e.g., 3O8 antibody), 135-140 (e.g., T2 antibody) or 132-147 (e.g., MA1-750 antibody), more preferably, antibodies to the epitopes of amino acids 109-112 (e.g., 3F4 antibody), 106-126 (e.g., 3O8 antibody) and 135-140 (e.g., T2 antibody), and most preferably, antibodies to the epitopes of amino acids 109-112 (e.g., 3F4 antibody) and 106-126 (e.g., 3O8 antibody). For example, a series of antibody sets of 3F4/3F4, 3F4/3O8, 3O8/3F4 or 3O8/3O8 for the capturing and detecting antibodies is very useful in the present method for human samples, in particular, plasma.

It is preferred that the capturing antibody and detecting antibody are identical to each other. That is, the epitopes specifically bound to the capturing antibody and detecting antibody are preferably the same.

According to a preferred embodiment, the capturing antibody is bound to a solid substrate. Known materials of this type include hydrocarbon polymers such as polystyrene and polypropylene, glass, metals, and gels. The solid substrate may be in the form of a dipstick, a microtiter plate, a particle (e.g., bead), an affinity column and an immunoblot membrane (e.g., polyvinylidene fluoride membrane) (see U.S. Pat. Nos. 5,143,825, 5,374,530, 4,908,305 and 5,498,551). Most preferably, the solid substrate is a microtiter plate.

According to a preferred embodiment, the detecting antibody has a label generating a detectable signal. The label includes, but not limited to, a chemical (e.g., biotin), an enzymatic (e.g., alkaline phosphatase, peroxidase, β-galactosidase and β-glucosidase), a radioactive (e.g., $I^{125}$ and $C^{14}$), a fluorescent (e.g., fluorescein), a luminescent, a chemiluminescent and a FRET (fluorescence resonance energy transfer) label. Various labels and methods for labeling antibodies are well known in the art (Harlow and Lane, eds. *Antibodies. A Laboratory Manual* (1988) Cold Spring Harbor Laboratory Press, Cold Spring Harbor, N.Y.). Most preferably, the detecting antibody is labeled with biotin or horseradish peroxidase.

In this invention, the antibody capable of binding to the multimer-forming polypeptide could be prepared using epitopes described previously as immunogens according to conventional techniques such as a fusion method (Kohler and Milstein, *European Journal of Immunology,* 6:511-519 (1976)), a recombinant DNA method (U.S. Pat. No. 4,816,56) or a phage antibody library (Clackson et al, *Nature,* 352:624-628(1991); and Marks et al, *J. Mol. Biol.,* 222:58, 1-597 (1991)). The general procedures for antibody production are described in Harlow, E. and Lane, D., *Antibodies. A Laboratory Manual*, Cold Spring Harbor Press, New York, 1988; Zola, H., *Monoclonal Antibodies. A Manual of Techniques*, CRC Press, Inc., Boca Raton, Fla., 1984; and Coligan, *CURRENT PROTOCOLS IN IMMUNOLOGY*, Wiley/Greene, N.Y., 1991. The preparation of hybridoma cell lines for monoclonal antibody production is done by fusion of an immortal cell line and the antibody producing lymphocytes. This can be done by techniques well known in the art. Polyclonal antibodies may be prepared by injection of the antigen described above to suitable animal, collecting antiserum containing antibodies from the animal, and isolating specific antibodies by any of the known affinity techniques.

"Biosample" is an organism-originated sample of material to be tested. The biosample refers to any cell, tissue, or fluid from a biological source, or any other medium that can advantageously be evaluated according to this invention, including a sample drawn from human, a sample drawn from an animal, a sample drawn from food designed for human or animal consumption. Preferably, the biosample to be tested is a body fluid sample including blood, serum, plasma, lymph, milk, urine, feces, ocular fluid, saliva, semen, brain extracts (e.g., brain homogenates), spinal cord fluid (SCF), appendix, spleen and tonsillar tissue extracts. More preferably, the biosample is a brain homogenate or plasma, most preferably, plasma.

Where the brain homogenate is used as a biosample, it is advantageous that the present method further comprises the step of treating the biosample with trypsin prior to step (a). The brain homogenate sample contains other proteins and materials to inhibit the binding of the aggregate-forming polypeptide of interest to the capturing antibody and/or detecting antibody. This matrix inhibition is prevented by the trypsinization. The advantage of the trypsin treatment is demonstrated in Example IV described hereunder. The proteinase K (PK) treatment conventionally used in prion detection processes is undesirable since PK digests $PrP^{Sc}$, being responsible for the possibility of the occurrence of false negative data. It is one of advantages of the present method to remove the need of the PK treatment which has been conventionally employed to discriminate $PrP^{Sc}$ from $PrP^{c}$. The present MDS method perse exhibits a sufficient potential to discriminate $PrP^{Sc}$ from $PrP^{c}$ without PK treatment.

Where the plasma is used as a biosample, the need for the proteinase treatment could be completely avoided as demonstrated in Example 10, being significant advantage of this invention.

According to a preferred embodiment, the present method further comprises treating the biosample with a protein denaturing agent prior to step (a). Such protein denaturing agent permits the epitope of the aggregate-forming polypeptide to be exposed, so that the binding of the capturing/detecting antibody to the aggregate-forming polypeptide is significantly enhanced. The protein denaturing agent may include any protein denaturant known in the art, for example, urea, tetramethylurea, guanidine hydrochloride, guanidine thiocynide and sodium dodecyl sulfate. Preferably, the protein denaturing agent is urea, guanidine hydrochloride and guanidine thiocynide, most preferably, guanidine hydrochloride. The concentration of protein denaturants, in particular, guanidine hydrochloride is in the range of 0.3-4 M, preferably, 0.3-3 M, more preferably, 0.5-2 M, and most preferably, about 1 M. The treatment time of protein denaturants, in particular, guanidine hydrochloride is in the range of 5-60 min, preferably, 10-50 min, more preferably, 10-40 min, and most preferably, 15-20 min.

According to a preferred embodiment, the present method further comprises heating the biosample prior to step (a). Where the brain homogenate is used as a biosample, the heating is performed at temperature of 70-100° C., preferably, 80-100° C., more preferably, 90-100° C., and most preferably, around 100° C. Where the plasma is used as a biosample, the heating is performed at temperature of 40-100° C., preferably, 50-80° C., more preferably, 60-80° C., and most preferably, approximately 70° C.

It is preferred that the biosample comprises a detergent. The detergent useful in the present method may include any known to one of skill in the art, preferably, sarkosyl (N-laurylsarcosine), Triton series such as Triton X-100 (polyoxyethylene alkyl phenols), sodium deoxycholate, zwitterionic surfactant such as zwittergent-16 and their combinations and more preferably, sarkosyl, Triton X-100, sodium deoxycholate, zwittergent-16 and their combination. Most preferably, the detergent contained in the biosample is a combination of Triton X-100 and sodium deoxycholate, where the brain homogenate is used as the biosample. Most preferably, the detergent contained in the plasma sample is a combination of sarkosyl, Triton X-100, sodium deoxycholate and zwittergent-16. The concentration of this detergent is at least 0.5% by weight, preferably, 0.5-3% by weight. Where the brain homogenate is used as the biosample, the concentration of detergents is 1.0-3.5% by weight, preferably, 1.5-3.0% by weight, more preferably, 2.0-3.0% by weight, and most preferably, about 2.5% by weight. The plasma sample contains lower concentration of detergents than the brain homogenate, preferably, 0.2-2.5% by weight, preferably, 0.3-2.0% by weight, more preferably, 0.5-1.5% by weight, and most preferably, about 0.6-1.0% by weight. Where the plasma is used as biosamples, the use of the sarkosyl detergent is advantageous since it contributes partially to the improvement in the final signal arising of the present process.

According to a preferred embodiment, the present method further comprises treating the biosample with an inhibitor to plasminogen prior to step (a) when the plasma is used as the biosample. The term "an inhibitor to plasminogen" used herein means a material to inhibit the activation of plasminogen, e.g., by streptokinase, urokinase or tissue activator. Such inhibition is generally achieved by blocking lysine binding sites on plasminogen involved in the binding between plasmin and fibrin monomer. More preferably, the inhibitor to plasminogen includes omega-aminocarboxylic acids [e.g., 4-aminobutyric acid, 5-aminopentanoic acid, 6-aminohexanoic acid (amino caproic acid, ACA), and 7-aminoheptanoic acid], L-lysine and derivatives ($N^{\alpha}$-acetyl-L-lysine, L-lysine-methyl ester, and $N^{\alpha}$-acetyl-L-lysine-methyl ester), Zwitterions [e.g., trans-(aminomethyl)cyclohexanecarboxylic acid (AMCHA), p-benzylaminesulfonic acid, and Zwitterionic gamma-guanidinobutyric acid), benzylamine, benzamidine, L-arginine and its derivatives (Nalpha-acetyl-L-arginine, Nalpha-acetyl-L-arginine methyl ester, and L-arginine methyl ester). Still more preferably, the inhibitor is aminocaproic acid or trans-(aminomethyl)cyclohexanecarboxylic acid, most preferably, trans-(aminomethyl)cyclohexanecarboxylic acid. The pretreatment of samples by the inhibitor to plasminogen enhances the differential detection of multimers (in particular, $PrP^{Sc}$) from monomers.

The detection of a multimeric form-detection antibody complex can be carried out by various processes well known in the art. The formation of a multimeric form-detection antibody complex is indicative of the presence of the multimeric form in biosamples. This step could be carried out quantitatively or qualitatively according to conventional procedures, e.g., using various detectable label/substrate pairs as described in *Enzyme Immunoassay*, E. T. Maggio, ed., CRC Press, Boca Raton, Fla., 1980 and Harlow and Lane, eds. *Antibodies. A Laboratory Manual* (1988) Cold Spring Harbor Laboratory Press, Cold Spring Harbor, N.Y.

Where the detecting antibody is labeled with alkaline phosphatase, bromochloroindolylphosphate (BCIP), nitro blue tetrazolium (NBT) and ECF may be used as a substrate for color developing reactions; in the case of labeled with horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), TMB (3,3,5,5-tetramethylbenzidine) and ABTS (2,2-Azine-di[3-ethylbenzthiazoline sulfonate]) may be used as a substrate. Other lable/substrate pairs include biotin/streptavidin, and luciferase/luciferin.

The present invention also encompasses the simultaneous use of various types of antibodies as capturing antibodies only if the cocktailed capturing antibodies are reactive epitopes identical to or overlapped with epitopes for a detecting antibody. As addressed in Example XI, the present invention using a cocktailed capturing antibody, e.g., 3O8 and 3F4, permits to differentially detect $PrP^{Sc}$ from $PrP^{c}$.

With reference to FIG. 1 representing a specific embodiment of this invention, the procedures of the present invention is described in more detail. Where a biosample containing isoforms of PrP such as $PrP^{Sc}$ and $PrP^{c}$ is applied to a microplate coated with capturing antibodies, both $PrP^{Sc}$ and $PrP^{c}$ are bound to the capturing antibodies. The epitope (depicted as a light trapezoid) specifically recognized by the capturing antibody is a non-repeated sequence in the prion protein. Afterwards, the HRP-labeled detecting antibody recognizing an epitope identical to or overlapped with the epitope to the capturing antibody is contacted with $PrP^{Sc}$ and $PrP^{c}$ captured by the capturing antibody. The detecting antibody is not bound to $PrP^{c}$ having only one epitope sequence since the epitope on $PrP^{c}$ is already covered by the capturing antibody. By contrast, the detecting antibody is bound to empty epitopes on $PrP^{Sc}$, since $PrP^{Sc}$ has a plurality of the epitopes. Following the treatment of the detecting antibody, microplates are washed and incubated with the substrate of HRP such as TMB (3,3,5,5-tetramethylbenzidine) to induce a calorimetric reaction. Finally, the absorbance at 450 nm is measured to determine whether the $PrP^{Sc}$-antibody complex is formed.

Alternatively, the present invention may be designed to perform an analysis process based on agglutination reaction. In such case, the present method comprises the steps of: (a) contacting the biosample to a capturing antibody recognizing an epitope on the multimer-forming polypeptide to capture said monomeric form, multimeric form or monomeric and multimeric forms, wherein the capturing antibody is bound to a solid carrier; and (b) determining the occurrence of agglutination between the capturing antibody bound to the solid carrier and the multimer-forming polypeptide, wherein the occurrence of agglutination is indicative of the presence of the multimeric form in the biosample.

Since the present agglutination process is a modification of the MDS process described above, the common descriptions between them are omitted so as to avoid undue redundancy leading to the complexity of this specification. For example, the descriptions for the multimer-forming polypeptide, capturing antibodies and biosamples are common between them.

According to a preferred embodiment, the solid substrate bound to capturing antibodies is a bead such as gelatin, latex, polystyrene and colloidal gold beads, more preferably, latex bead. The size of these carries may be selected from the range of 0.3 nm to 20 μm in diameter, and an optimal size can be selected according to the evaluation method of agglutination to be used. For example, for macroscopic evaluation of agglutination, it is desirable to employ carriers of 0.2 to 3 μm in diameter with which macroscopic judgment is easier.

Figure 2:
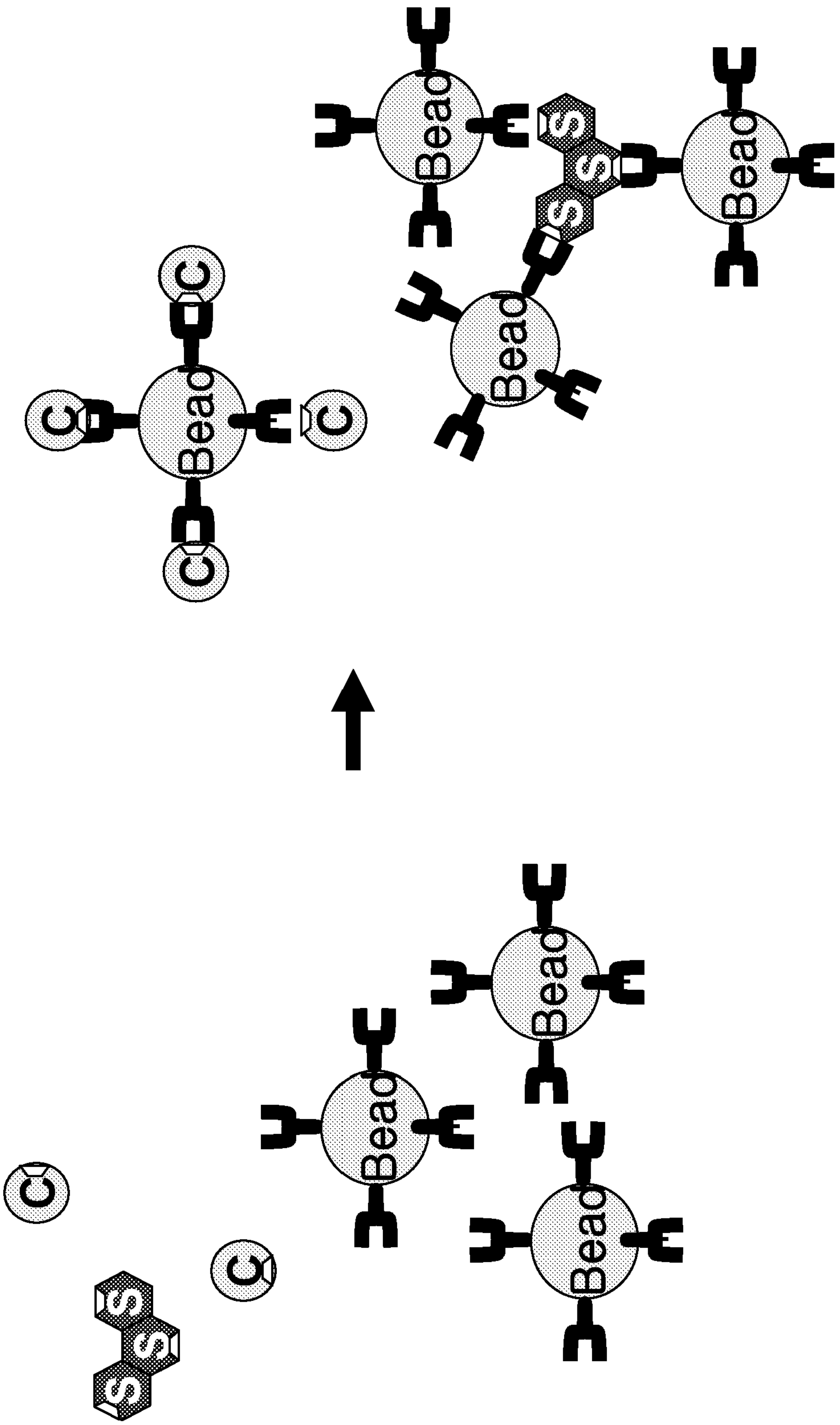
FIG. 2 schematically represents the processes of a specific embodiment of this invention based on agglutination.

With reference to FIG. 2 representing a specific embodiment, the present agglutination process will be described in more detail. Beads as solid substrates are coated with antibodies to bind to an epitope (preferably, non-repeated epitope) on the prion protein. Where beads are contacted to a biosample containing $PrP^{Sc}$ and $PrP^{c}$, both $PrP^{Sc}$ and $PrP^{c}$ are bound to antibodies combined with beads. Moreover, $PrP^{Sc}$ carrying a plurality of the epitope is bound to antibodies on several beads to form a complex of $PrP^{Sc}$/beads, leading to agglutination. However, $PrP^{c}$ does not generate the agglutination since $PrP^{c}$ has one epitope. The occurrence of agglutination may be readily determined in accordance with conventional methods known to one skilled in the art.

In summary, the prominent advantages of the present invention will be described as follows:

(i) The MDS requires no multimer-specific antibodies. For example, it is not dependent on $PrP^{Sc}$-specific antibodies. Antibodies having cross-reactivity between $PrP^{Sc}$ and $PrP^{c}$ can be successfully applied to the present invention for differentially detecting $PrP^{Sc}$ in biosamples;

(ii) The present invention does not need proteinase K (PK) treatment having been conventionally used for $PrP^{Sc}$ detection. The present MDS method per se exhibits a sufficient potential to discriminate $PrP^{Sc}$ from $PrP^{c}$ without PK treatment;

(iii) The present invention enables aggregating forms (particularly, $PrP^{Sc}$) in plasma samples to be detected by immunoassay. Little has been suggested about successful detection of $PrP^{Sc}$ in plasma; and, (iv) The present invention can carried out in a convenient and speedy manner, which enables the automation of the MDS.

The following specific examples are intended to be illustrative of the invention and should not be construed as limiting the scope of the invention as defined by appended claims.

EXAMPLES

Materials:

3F4 and 3F4-Biotin antibodies were purchased from Sigma (US) and Abcam Ltd (UK), respectively. 3O8 and MA1-750 antibodies were purchased from Cayman Chemical Co. and Affinity BioReagents Inc. (US). T2-HRP and 1F5 antibodies were gift from National Institute of Animal Health (Japan). Bovine and hamster recombinant (23-231) prion proteins were purchased Prionics AG. (CH) and Alicon AG (CH), respectively. Mouse and human recombinant (23-231) prion proteins were gifts from University of Maryland and National Institute of Animal Health (Japan). Age matched normal and scrapie hamster brain homogenates were purchased from SLC, Inc. (Japan) and Baltimore Research and Education Foundation, respectively. HRP-conjugated anti-mouse IgG and the enhanced chemiluminescence kit were purchased from Amersham Biosciences (UK). PVDF membrane was purchased from Bio-Rad Inc. (US). Startingblock was purchased from Pierce Biotechnology Inc. (US). X-ray film was purchased from Fuji Inc. (Japan). Chemiluminescent HRP substrate, Supersignal West Pico was from Pierce Biotechnology Inc. (US). TMB was from Sigma (US). Purified mouse $PrP^{Sc}$ from brain homogenate was the gift from National Institute of Animal Health (Japan). Trypsin was purchased from Fluka (US). Protease Inhibitor cocktail was from Sigma (US).

Example I

Western Blot Analysis of Recombinant Prion Protein 0.2 ng of recombinant bovine prion protein (PrP 23-231 from University of Maryland) was loaded into native gel (12.5% SDS-PAGE) without denaturant and the contents of the gel were transblotted to PVDF membrane (Bio-Rad) over 12 hr at 4° C. The PVDF blot was blocked with 50% Startingblock (PIERCE) in TBS. Afterwards, 6H4 antibody (Prionics AG) was used as primary antibody and HRP-linked anti-mouse IgG (Amersham) was used as secondary antibody for the detection. The enhanced chemiluminescence (ECL) detection was used to developed the blot by exposing to X-ray film (Fuji). Prion multimers, as dimer, trimer, and higher molecular bands, were detected.

Figure 3:
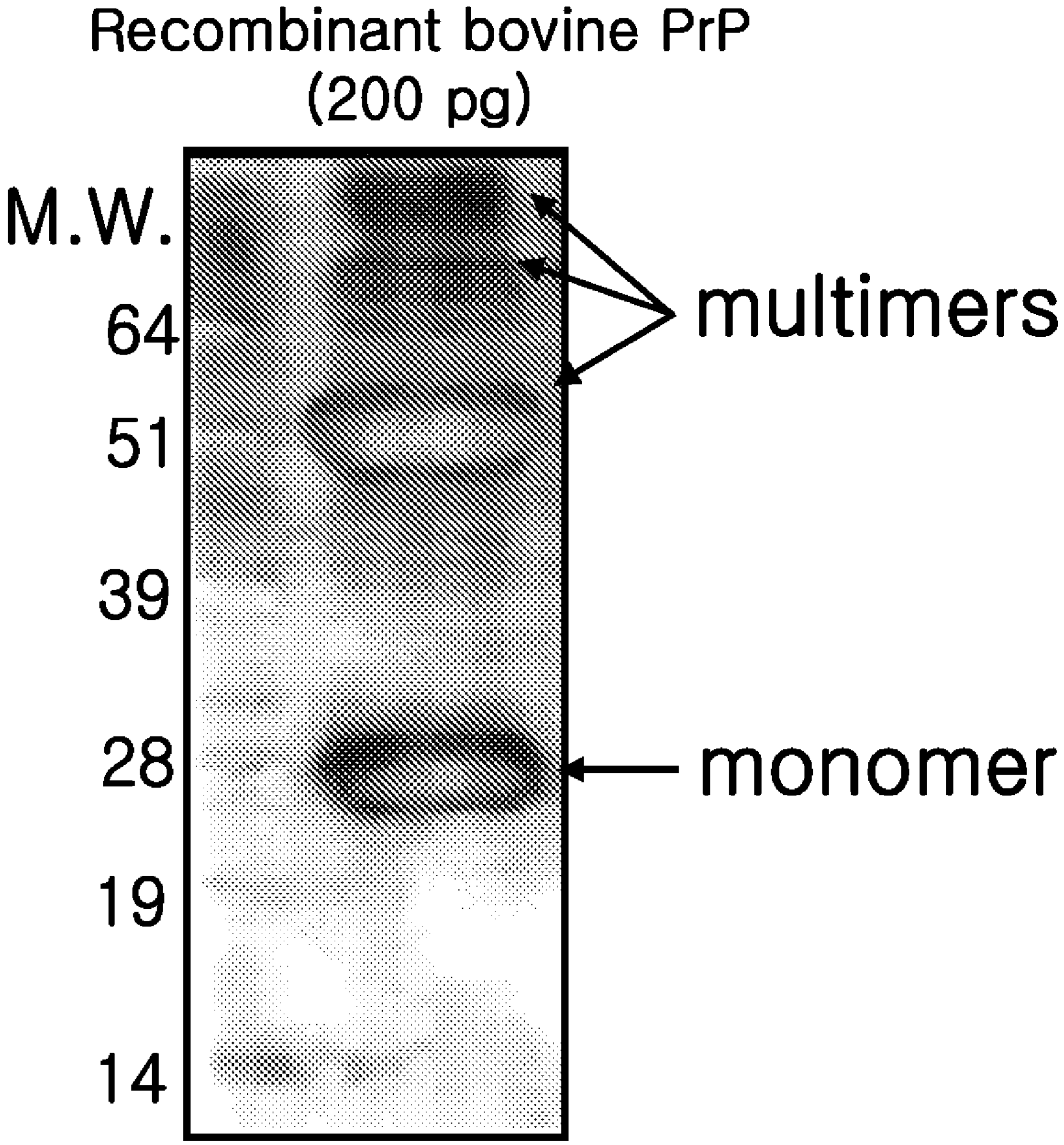
FIG. 3 shows the results of Western blotting analysis of recombinant bovine prion proteins.

As shown in FIG. 3, the results indicate that various prion multimers and monomer exist in the recombinant bovine prion protein sample and can be detected by 6H4 anti-prion antibody.

Example II

Evaluation on Workability of MDS for Detecting $PrP^{Sc}$

MA1-750 antibody coated plates were prepared. 30 μg of MA1-750 antibody (anti-prion protein, Affinity Bioreagents, Inc.) was suspended in 10 μl of 200 mM MOPS and aliquoted in a volume of 100 μl into each well of immuno module plates (Nunc-468667), followed by overnight incubation at 4° C. The plates were washed with PBS and blocked for 1 hr with ovalbumin in PBS at room temperature.

10% bovine brain homogenate in 4% zwittergent (Anaphase Inc., US) was serially diluted by 4-fold, aliquoted into MA1-750 antibody coated plates and then incubated for 1 hr at 37° C. MA1-750 antibody recognizes specifically an epitope on $PrP^c$, Ser-Arg-Pro-Leu-Ile-His-Phe-Gly-Ser-Asp-Tyr-Glu-Asp-Arg, which is found to be a non-repeated sequence in prion. The plates were washed five times with TBST and incubated with MA1-750-HRP (1:2000 in TBST) for 1 hr at 37° C. After the incubation, the plates were washed with PBS and the HRP activities were quantitated by incubating for 30 min with HRP substrate, 3,3,5,5-tetramethylbenzidine (TMB, SIGMA Inc.). The color development signal was measured at 450 nm using SpectraMax $Plus^{384}$ (Moledular Device Inc.).

For comparison, an enzyme immunoassay kit for $PrP^c$ commercially available from SPIbio, Inc.(Cat. No. A05201) was employed. 10% bovine brain homogenate in 4% zwittergent (Anaphase Inc., US) was serially diluted by 4-fold, aliquoted into MA1-750 antibody coated plates and then incubated for 1 hr at 37° C. The plates were washed five times with TBST and incubated with anti-prion tracer (recognizing the octo-repeat sequence in N-terminal of $PrP^c$) contained in the SPIbio's kit for 1 hr at 37° C. The plates were then washed with SPIbio's washing buffer and incubated with 200 μl of Ellman's reagent for 30 min for color development. The color development signal was measured at 400 nm using SpectraMax $Plus^{384}$ (Moledular Device Inc.).

TABLE 1

| Conc. of bovine brain | OD | |
|---|---|---|
| homogenate (%) | MDS | SPIbio kit |
| 0.5 | 0.1206 | 1.0909 |
| 0.13 | 0.0928 | 0.4879 |
| 0.03 | 0.0719 | 0.2328 |
| NSB | 0.0923 | 0.1153 |
| Background | 0.0839 | 0.0839 |

In Table 1, NSB (non-specific binding) represents an experiment set without bovine brain homogenate and background represents an experiment set using only a color development substrate without antibody incubation.

Figure 4:
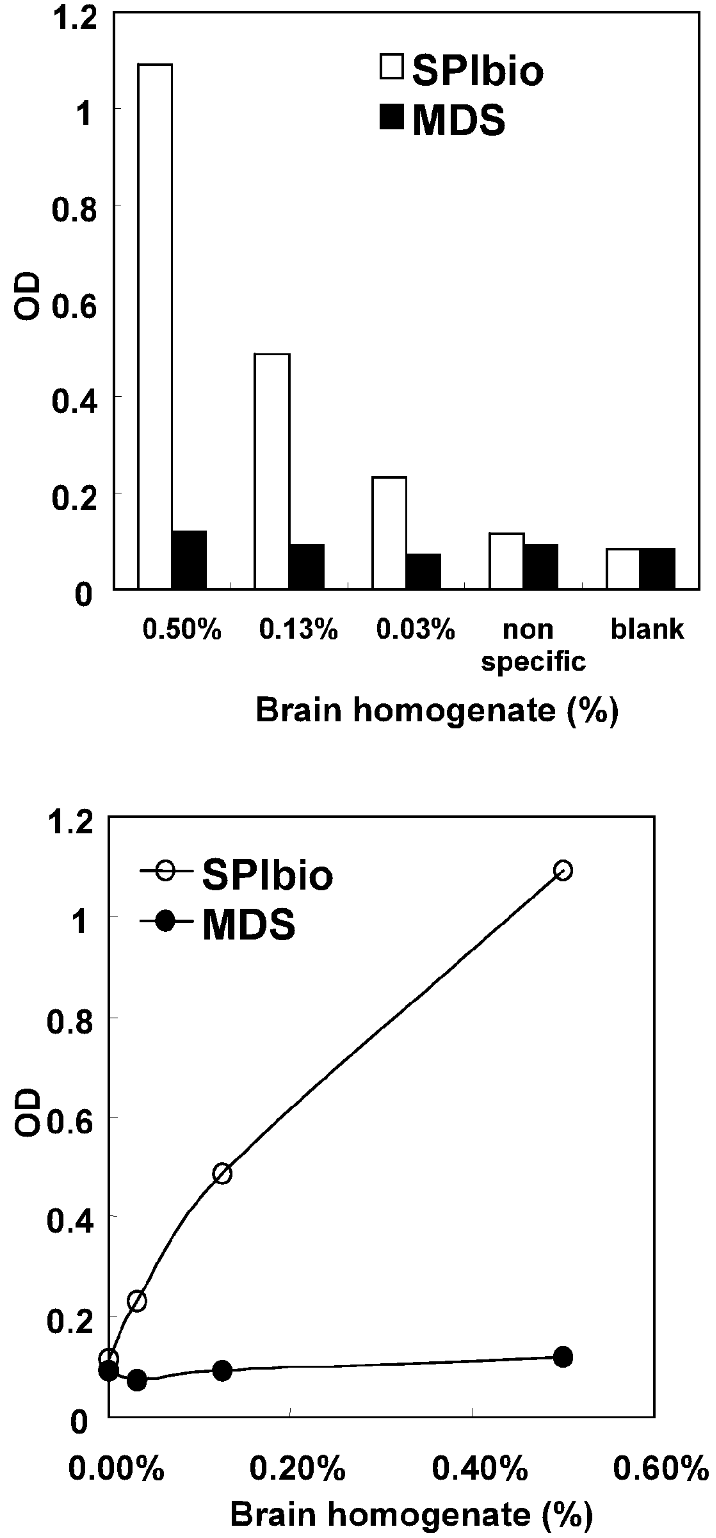
FIG. 4 is graphs to show the analysis results for prion proteins (PrP) by either conventional process (SPIbio) or present process (MDS), demonstrating the present method allows to differentially detect the multimeric (scrapie) form of prion ($PrP^{Sc}$).

As addressed in Table 1 and FIG. 4, the MDS of this invention was revealed to completely exclude the involvement of $PrP^c$ in the final color signal. Such result is ascribed to a dual employment of MA1-750 as both capturing and detecting antibodies, which is a striking feature of this invention. In addition, such discrimination potency of the MDS is due partly to the fact that the epitope recognized by MA1-750 is a non-repeated sequence in prion. In contrast, the SPIbio's kit exhibits higher OD values, demonstrating the contribution of $PrP^c$ to the final color signal result.

Consequently, it would be appreciated that the MDS of this invention permits to detect specifically $PrP^{Sc}$ in samples.

Example III

Detection of Multimeric Forms of Prion Protein by Agglutination

A recombinant bovine prion protein in a multimeric form was prepared. 3.1 μg of recombinant bovine prion protein was dissolved in 700 μl of a coupling buffer (5 mM potassium phosphate, 75 mM NaCl, pH 6.5) and reacted with EDC [1-ethyl-3-(3-dimethylaminopropyl)carbodiimide, Sigma E6383) solution for 24 hr at room temperature.

Latex beads were coated with MA1-750 antibody. 70 μl of MA1-750 antibody was mixed with 4 ml of the coupling buffer (5 mM potassium phosphate, 75 mM NaCl, pH 6.5) and centrifuged for concentration. 70 μl of latex beads (Carboxylate modified Latex beads, Sigma L5530) was centrifuged for precipitation and the resulting supernatant was discarded, to which the coupling solution was added. 70 μl of the bead suspension was mixed with EDC solution and incubated with 70 μl of the concentrated MA1-750 antibody, followed by 24-hr incubation at room temperature. The coated beads were precipitated by centrifugation, resuspended with a washing buffer (10 mM Tris, 150 mM NaCl, 1 mM EDTA, 0.1% ovalbumin, pH 7.5) and re-precipitated. The precipitated beads were dissolved in 70 μl of PBS.

Afterwards, 10 μl of the MA1-750-coated latex beads was mixed with 10 μl of 1% bovine brain homogenate treated or non-treated with EDS, or 45 ng of recombinant bovine prion protein treated or non-treated with EDS, after which the resultant was observed under a fluorescence microscope (×400, Carl Zeiss Axiovert 100).

As a result, it was observed that a very slight agglutination occurred in bovine brain homogenates without regard to EDC treatment. The slight agglutination may be ascribed to a multimeric prion formed from a minute amount of $PrP^{Sc}$ present in bovine brain homogenates. In contrast to this, the recombinant prion protein was observed to be agglutinated only in multimeric prion samples treated with EDC.

Consequently, it could be recognized that the agglutination process of this invention allows for the differential detection of $PrP^{Sc}$ in samples.

Example IV

Detection of $PrP^{Sc}$ Multimers in Hamster Brain Homogenate

Hamster scrapie brain homogenate (10% by weight) was purchased pre-made. The age matched normal brain homogenate (10% by weight) was made using PBS and homogenizer. The brain homogenate was digested with trypsin (5 mg/ml) for 1 hr at 37° C. and the trypsin digestion was stopped by Protease inhibitor cocktail. The sample was treated with 8 M guanidine hydrochloride (Sigma, Gdn-HCl) to yield 1.0 M, followed by 15 min incubation at ambient temperature. Then, the sample was further diluted to yield 0.25 M Gdn-HCl with TBST, 2 % Triton X-100 and 0.5% Na deoxycholate. The sample was heated for 5-10 min at 100° C. After the sample reached the ambient temperature, the samples were applied to MDS. For the MDS set, T2 coated on plate was used as a capturing antibody and T2-HRP as a detection antibody.

100 μl of the samples were applied to T2 coated plate and incubated at 37° C for 1 hr with shaking. Followed by washing with TBST (four times), 100 μl of T2-HRP (1 μg/ml) was applied for the detection of the captured multimers on T2 coated plate. The plate was incubated at ambient temperature for 1 hr, and was washed four times with TBST. 100 μl of TMB was added to the each well and kept for 30 min to develop the signal. 50 μl of 1 N $H_2SO_4$ was added to stop the signal, and plate was read with the plate spectrophometer at 450 nm.

Figure 5:
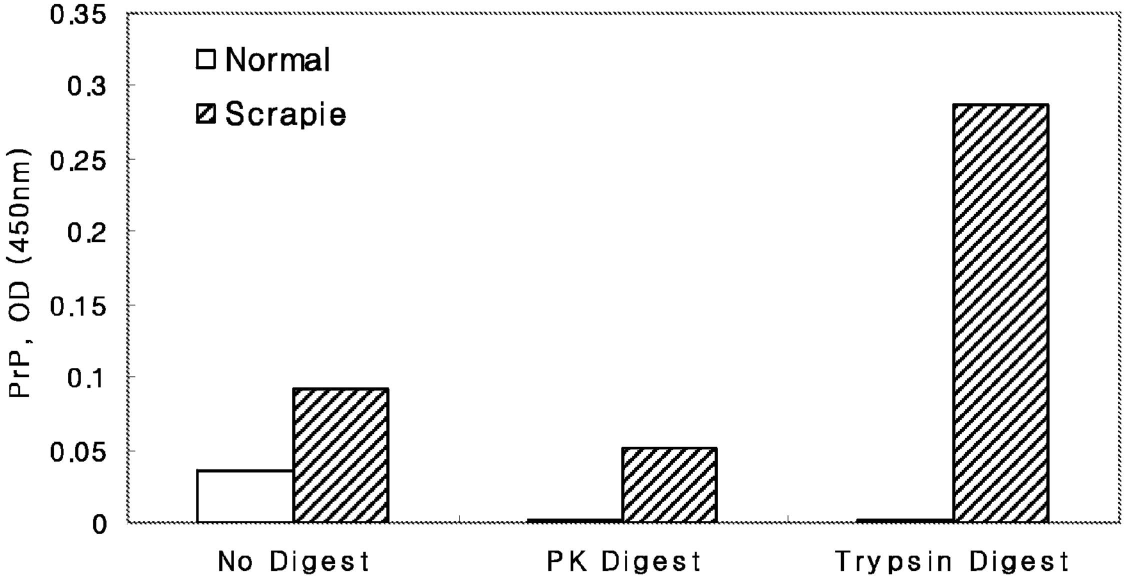
FIG. 5 represents the results of detecting $PrP^{Sc}$ multimers in hamster brain homogenates in accordance with the present invention. Hamster brain homogenates were obtained using different proteinases (proteinase K and trypsin).

As shown in FIG. 5, a much higher signal was observed from the scrapie hamster brain homogenate than the normal sample. Proteinase K or trypsin treatments resulted in complete digestion of the normal $PrP^c$. A signal differentiation between normal and scrapie samples became greater using proteinase K or trypsin digestions. It was observed that the scrapie sample was partially digested by proteinase K, being responsible for false negative results in proteinase K-involved prion assay methods as discussed in previous publications. By contrast, the trypsin treatment was revealed not to digest the scrapie form and resulted in the significantly improved detection of $PrP^{Sc}$. $PrP^{Sc}$ (multimers) was detected in hamster scrapie brain homogenate by the MDS and not in normal hamster samples.

Example V

Preparation of Plasma

Blood samples were drawn from normal or sporadic CJD patients into Na-Citrate, EDTA and Heparin tubes, preferably into heparin. For obtaining plasma, normal plasma collection procedure was applied. The tubes were centrifuged at 1000×g and/or 2800×g for 10-15 min. The clear supernatant (plasma) was separated and stored at −80° C until usage. Age-matched normal and scrapie infected hamster plasmas were obtained from the pool of more than 5 animals into Na-Citrate tubes. Plasma was obtained as described above. For the plasma sample treatment for the MDS, the plasma was mixed with guanidine hydrochloride (Sigma, Gdn-HCl), to yield the final concentration of 1-2 M and incubated at room temperature or 37° C. for 15-60 min. The sample was diluted with TBS or PBS buffers containing detergents, 0.02% sarkosyl (Sigma), 0.5% Triton X-100 (Samchun Chemical), 0.125% sodium deoxycholate (Sigma) and 0.5% or 1% zwittergent-16 (Anaphase Inc., US), and incubated for 15 min at room temperature or 37° C. for 15-60 min to have the final concentration of denaturant at 0.125-0.5 M. The samples were then heated to 70° C. for 10-15 min and were kept to reach room temperature.

Example VI

Control ELISA for $PrP^{Sc}$ for Total PrP Concentration

The antibody coated plates were prepared by the following conventional method. The epitopes for 3O8 (Cayman) and 3F4 (Sigma) are over-lapping, where KTNMKHMAGAAAAGAVVGGLG (106-126) and MKHM (109-112) are specific epitopes, respectively. For the detection of total prion proteins in human plasma by the Control ELISA, 3O8, 3F4, or combination of 3O8 and 3F4 were coated onto 96-well polystyrene microtiter plate (NUNC) using the coating buffer (BupH Carbonate-Bicarbonate; PIERCE) with concentration of 1-5 μg/ml. The plates were incubated overnight at 4° C. and blocked with Startingblock (PIERCE) or Block Ace (Serotec) in TBS or PBS (pH 7.4) for 30-60 min at room temperature.

For the detection of total prion proteins in mouse and bovine plasmas by the Control ELISA, 1F5 anti-prion antibody was used as capturing antibody with T2-HRP as detection antibody. Since 3F4 and 3O8 did not bind to prion protein from mouse or bovine, 1F5 antibody which can bind to mouse and bovine prion proteins, was used.

The plasma samples were obtained from wild-type and PrP knock-out mice to detect mouse prion, and normal human to detect human prion. The plasma samples were aliquoted onto plates coated with antibodies and incubated for 60 min or longer at 37° C. Afterwards, the plates were washed four times with TBS containing 0.05% Tween 20 (Sigma). The detection antibody, T2-HRP or 5G12-biotin (225-228), in 1-5 μg/ml concentration was added to the wells, followed by 1 hr incubation at 37° C. The plates were again washed and the total PrP were detected streptavidin/biotin/HRP detection system. 100 μl of streptavidin (2 μg/ml, Promega), diluted in TBST, were added to the wells, and incubated for 1 hr at ambient temperature. Afterwards, the plates were washed four times with TBS containing 0.05% Tween 20 (Sigma). Biotin-HRP (Molecular Probes) was diluted in 10% Startingblock (PIERCE) with TBST (Sigma) to 1 μg/ml, and 100 μl were added to each well. After 1 hr incubation at ambient temperature, the plates were washed four times with TBS containing 0.05% Tween 20 (Sigma). TMB (100 μl, Sigma) was added to the wells and the signals were developed for 30 min. 1 N $H_2SO_4$ (50 μl) was added to stop the signal development and read at 450 nm in the plate spectrophotometer. Since HRP was used, many HRP substrates could be used for optical density, fluorescence, chemiluminescence, radio-isotope, electrochemical detection methods.

Figure 6A:
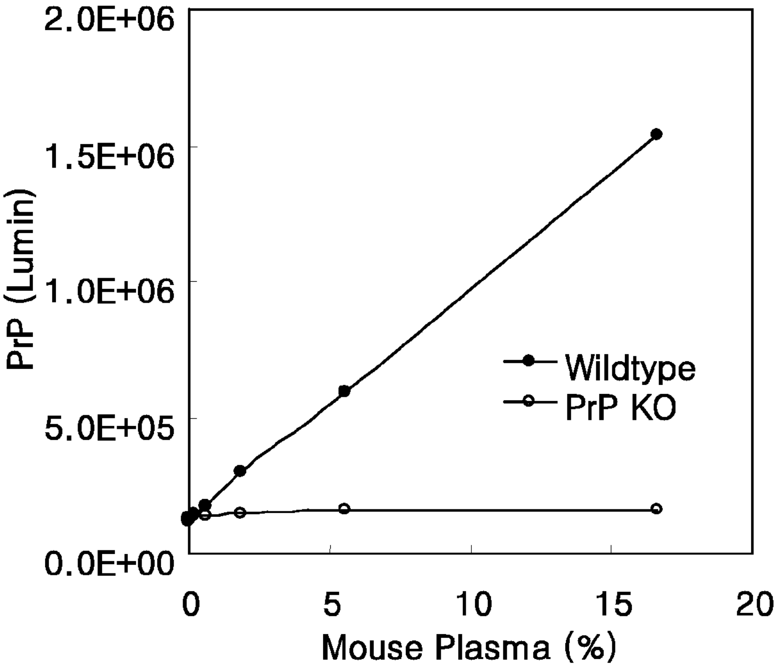
FIG. 6*a* represents the results of the Control ELISA for analyzing the total PrP concentration. Plasma samples from wild type and PrP knock-out (PrP KO) mice were used.
Figure 6B:
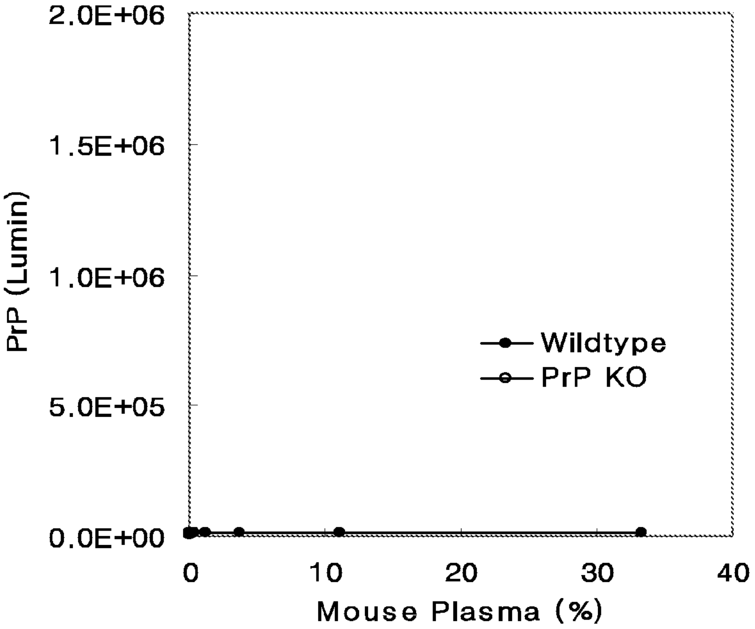
FIG. 6*b* represents the results of the present process for detecting the multimeric form ($PrP^{Sc}$) of prion in plasma samples from wild type and PrP knock-out (PrP KO) mice.
Figure 6C:
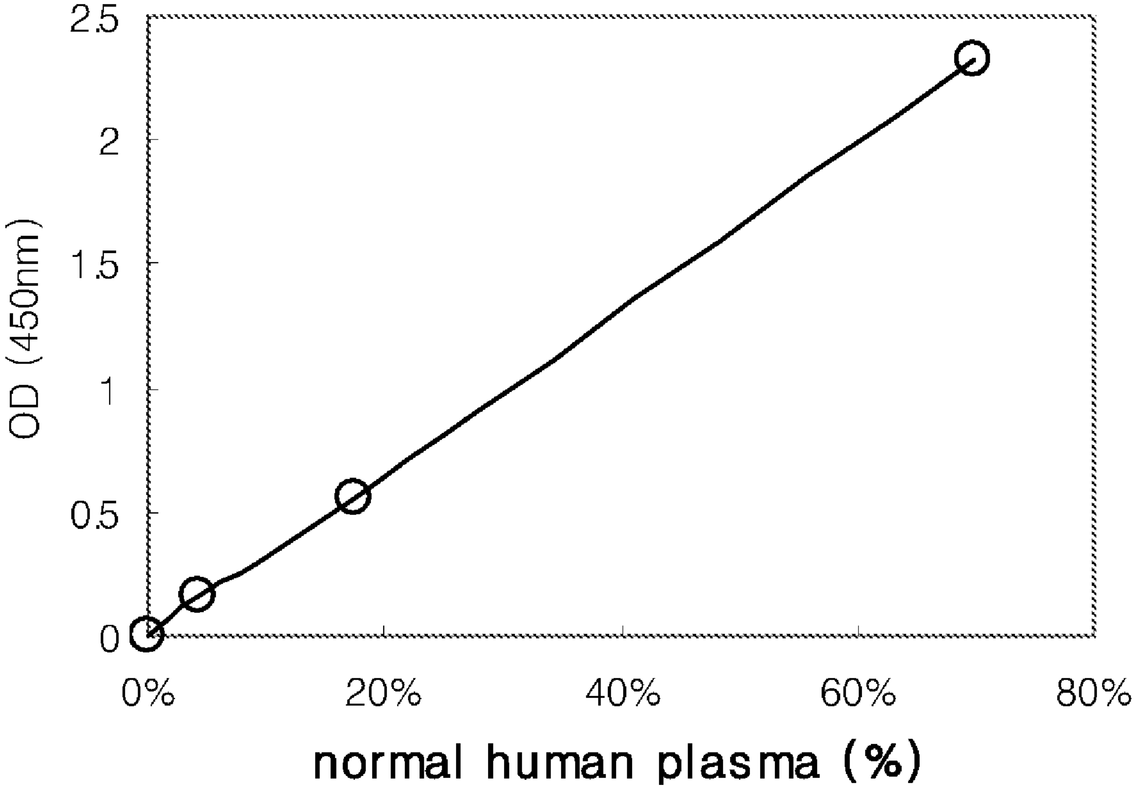
FIG. 6*c* represents the results of the Control ELISA for analyzing the total PrP concentration in normal human plasma.

As shown in FIG. 6*a*, the Control ELISA system generates a signal in a concentration-dependent manner from plasma samples obtained from wild-type mouse but no signal from PrP knock-out mouse not bearing prion proteins. Furthermore, in experiments following the MDS of this invention using MA1-750 and T2-HRP as capturing and detecting antibodies, respectively, no signal was observed for plasma samples from wild-type and PrP knock-out mice because the plasma samples did not contain the multimeric forms, $PrP^{Sc}$ (see FIG. 6*b*). The Control ELISA system also shows concentration-dependent signals from normal human plasma (see FIG. 6*c*).

Example VII

MDS for Detection of $PrP^{Sc}$ in Recombinant Prion Proteins

MA1-750 antibody was used as a capturing antibody and T2-HRP as a detection antibody for the detection of $PrP^{Sc}$ in recombinant prion proteins from bovine and mouse. 3O8 and 3F4-biotin antibodies were used as a capturing antibody and detection antibody, respectively, for the detection of $PrP^{Sc}$ in human recombinant prion proteins.

The recombinant prion protein samples were diluted with TBS containing 0.05% Tween 20 (Sigma) and aliquoted with concentrations in 3-fold dilutions, 2, 0.67, 0.22, 0.07, 0.02, 0.01 and 0 μg/ml, onto plates coated with the capturing antibody and incubated for 60 min or longer at 37° C. Afterwards, the plate was washed four times with TBS containing 0.05% Tween 20 (Sigma). The detection antibody, in 1-5 μg/ml concentration was added to the wells, followed by 1 hr incubation at 37° C. The plates were again washed and the multimers were detected using Streptavidin/biotin/HRP detection system. 100 μl of streptavidin (2 μg/ml, Promega), diluted in TBST, were added to the wells, and incubated for 1 hr at ambient temperature. Afterwards, the plates were washed four times with TBS containing 0.05% Tween 20 (Sigma). Biotin-HRP (Molecular Probes) was diluted in 10% Startingblock (PIERCE) with TBST (Sigma) to 1 μg/ml, and 100 μl were added to each well. After 1 hr incubation at ambient temperature, the plates were washed four times with TBS containing 0.05% Tween 20 (Sigma). TMB (100 μl, Sigma) was added to the wells and the signals were developed for 30 min. 1 N $H_2SO_4$ (50 μl) was added to stop the signal development and the absorbance was measured at 450 nm in the plate spectrophotometer. Since HRP was used, many HRP substrates could be used for optical density, fluorescence, chemiluminescence, radio-isotope, electrochemical detection methods. Since HRP was used, many HRP substrates could be used for the detection of the changes in optical density, fluorescence, chemiluminescence, radio-isotope, electrochemical detection methods.

Figure 7A:
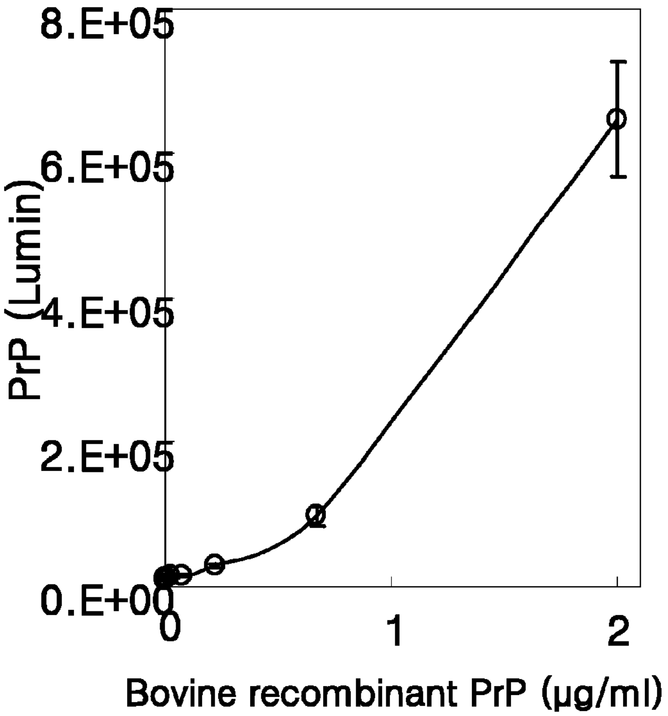
FIGS. 7*a*-7*c* represent the results of the present process for detecting the multimeric form ($PrP^{Sc}$) of prion in bovine, mouse and human recombinant prion protein samples, respectively.
Figure 7B:
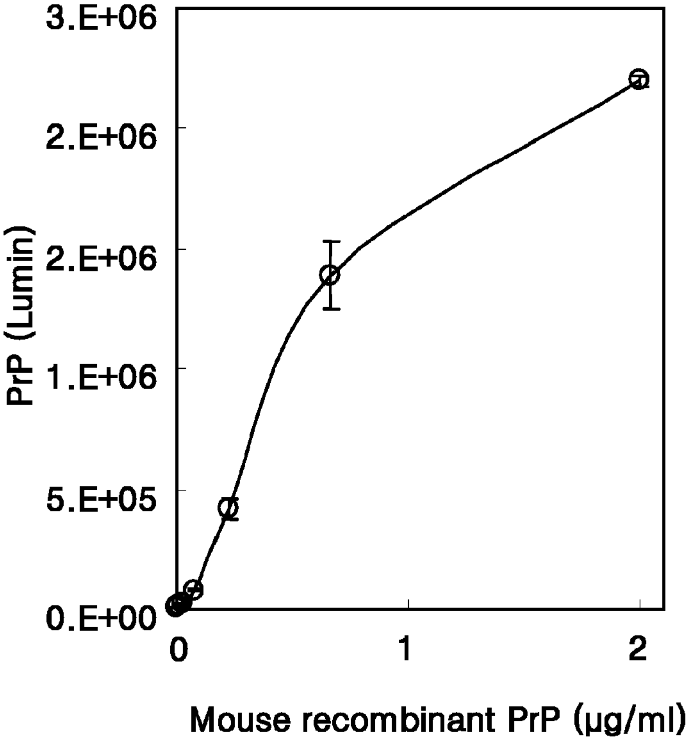
Figure 7C:
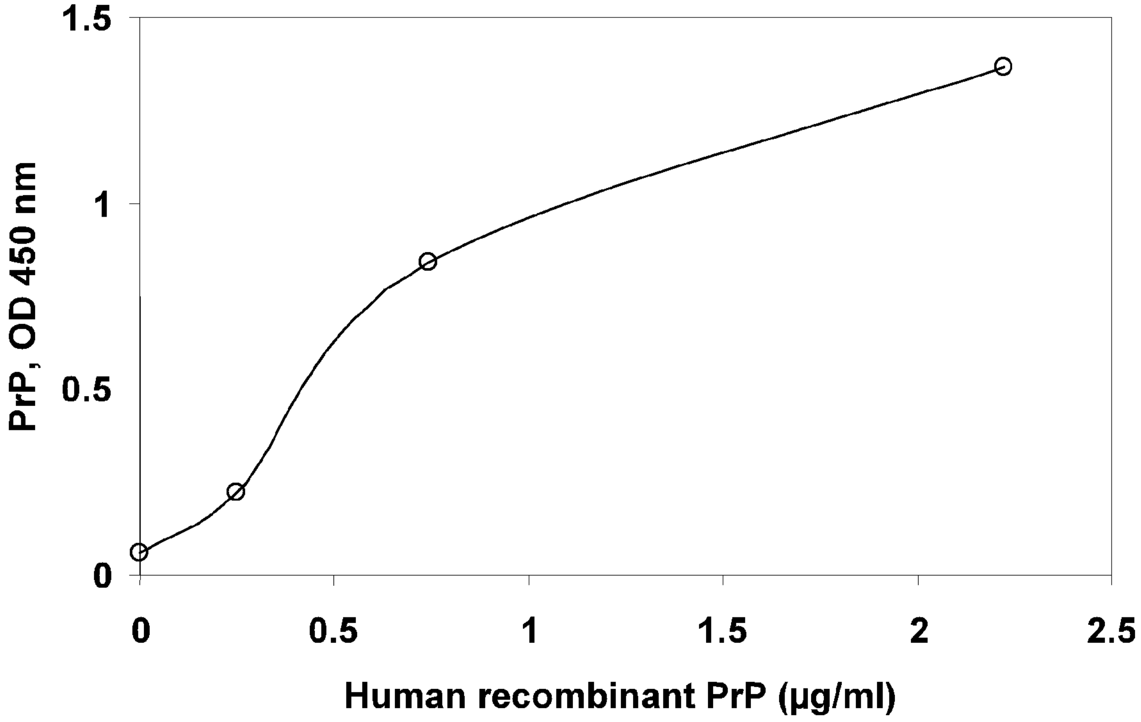

As shown in FIGS. 7*a*-7*c*, the multimers were detected in bovine, mouse and human recombinant prion protein samples by the MDS method in a concentration-dependent manner, consistent with the Western blot results of Example I.

Example VIII

Detection of Purified $PrP^{Sc}$ from Mouse Brain Spiked into Bovine Plasma

The purified $PrP^{Sc}$ (multimeric form of prion) from scrapie mouse brain was spiked into 100% bovine plasma and applied to the MDS by following the above MDS protocol. Briefly, 1.25, 0.42, 0.14, 0.05, 0.02 and 0% purified $PrP^{Sc}$ were diluted into 100% bovine plasma, yielding approximately 3.125, 1.04, 0.35, 0.12, 0.04, 0.01 and 0 μg/ml. 100 μl of the spiked plasmas were incubated onto MA1-750 coated plates for 1 hr at 37° C. After washing the plate four times with TBST, the T2-HRP detection antibody was added, followed by 1 hr incubation at ambient temperature. The plate was washed four times with TBST and TMB was added to develop the signal for 30 min. The stopping solution (50 μl of 1 N $H_2SO_4$) was added and the plate was read at 450 nm.

Figure 8:
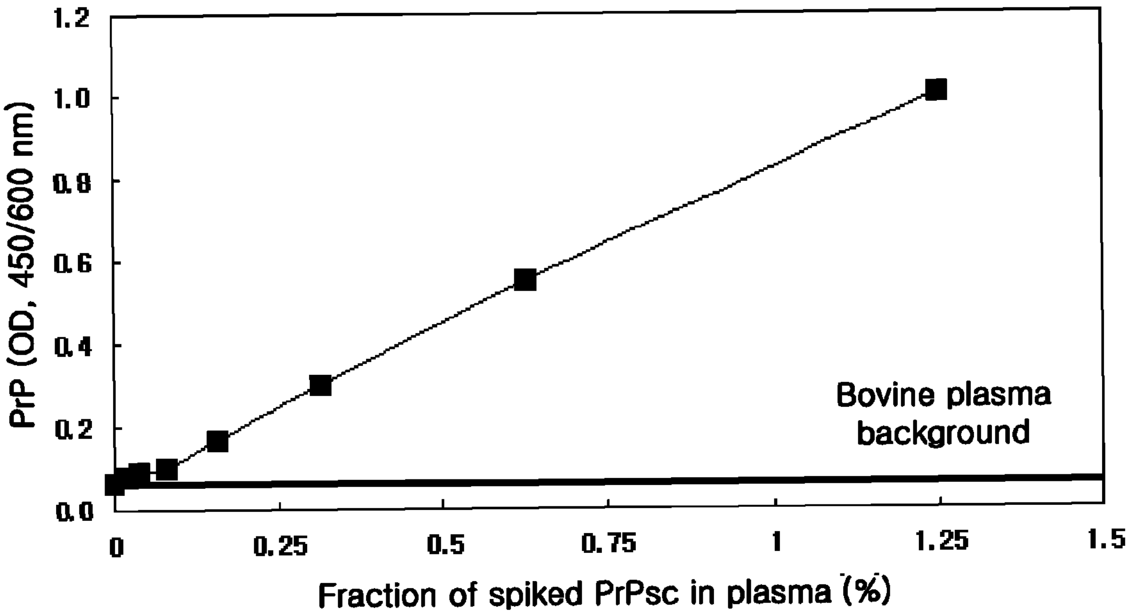
FIG. 8 is a graph showing the results of the present method for detecting the multimeric form ($PrP^{Sc}$) of prion spiked into bovine plasma.

The results show that purified $PrP^{Sc}$ (multimeric form of prion) from scrapie mouse brain in 100% bovine plasma was detected by MDS in a concentration-dependent manner, as shown in FIG. 8. Bovine plasma sample without purified $PrP^{Sc}$ from scrapie mouse brain did not show any signal.

Example IX

Concentration of Bovine Plasma

The purpose of this experiment was to detect any prion multimer in bovine plasma after concentration. Bovine plasma was concentrated using Amino Centrifuge concentrator to 200, 400, and 500%. The concentrated samples were analyzed by both Control ELISA and MDS by following the above protocols. A set of MA1-750 and T2-HRP was used for MDS and a set of 1F5 and T2-HRP for Control ELISA.

Figure 9:
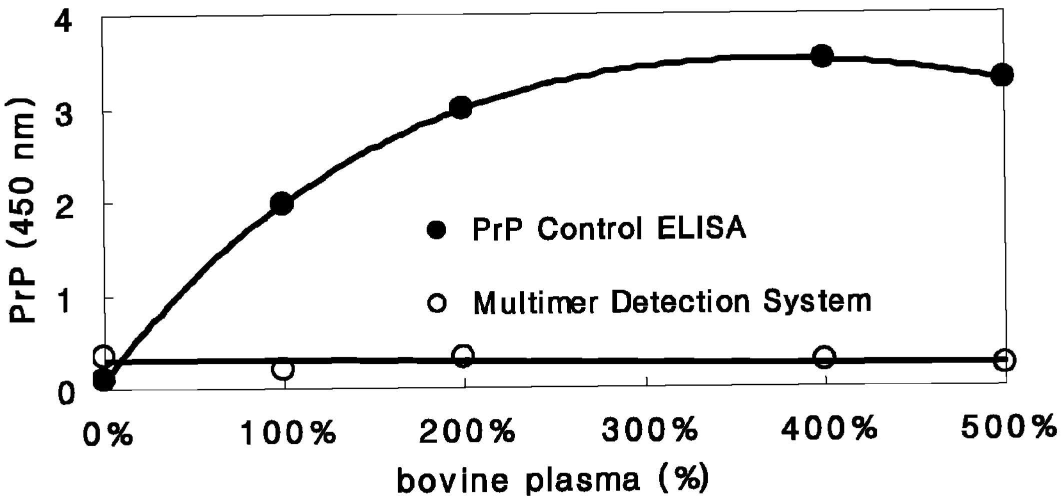
FIG. 9 represents the results of experiments according to the Control ELISA and the present process (Multimer Detection System) for normal bovine plasma concentrated.

As represented in FIG. 9, prion in bovine plasma was detected in the Control ELISA; however, no signal was observed in MDS in various plasma concentrations, suggesting that prion proteins in normal bovine plasma exist as a monomeric form.

Example X

Detection of $PrP^{Sc}$ in Plasma

3O8 antibody was used as a capturing antibody and 3F4-biotin as a detection antibody. The plasma samples were aliquoted onto plates coated with 3O8 (Cayman) and incubated for 60 min or longer at 37° C. Afterwards, the plate was washed four times with TBS containing 0.05% Tween 20(Sigma). The detection antibody, 3F4-biotin, in 1-5 μg/ml concentration was added to the wells, followed by 1 hr incubation at 37° C. The plates were again washed and the multimers were detected using streptavidin/biotin/HRP detection system as described above. Since HRP was used, many HRP substrates could be used for the detection of the changes in optical density, fluorescence, chemiluminescence, radio-isotope, electrochemical detection methods.

Figure 10A:
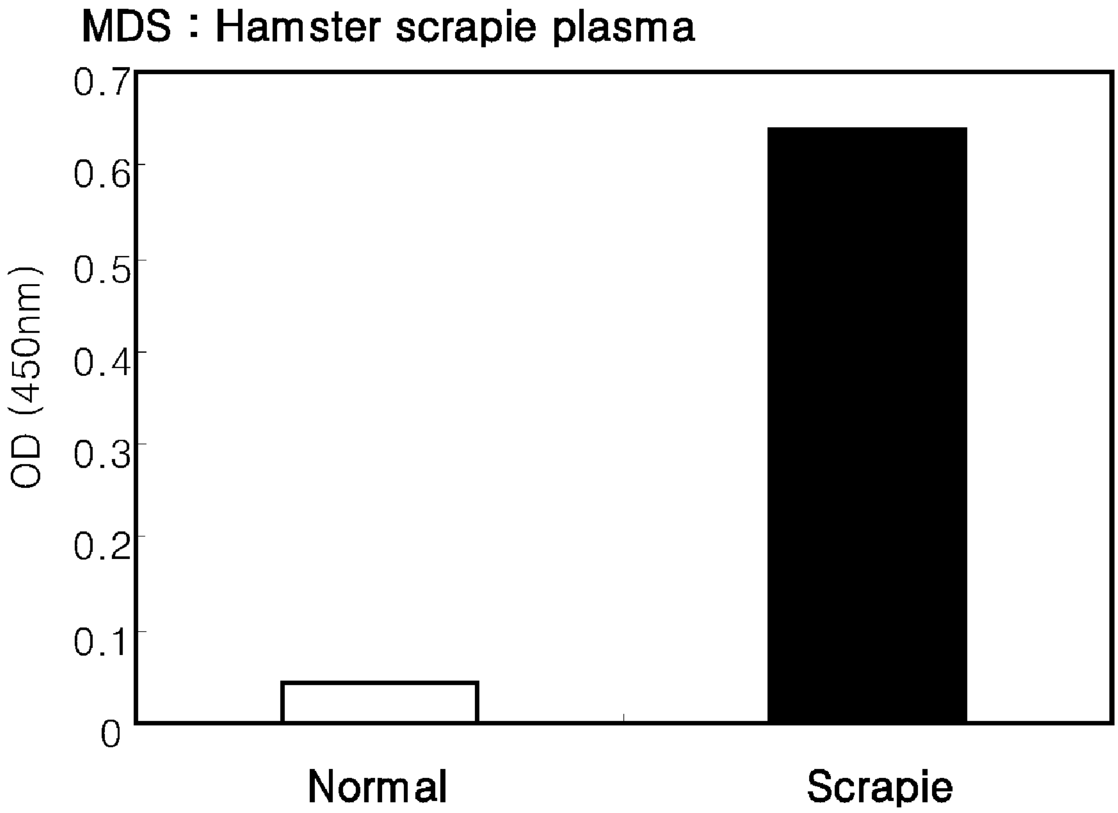
FIG. 10*a* shows the analytical results of the present process for detecting the multimeric form ($PrP^{Sc}$) of prion in plasma samples from normal or scrapie hamster.
Figure 10B:
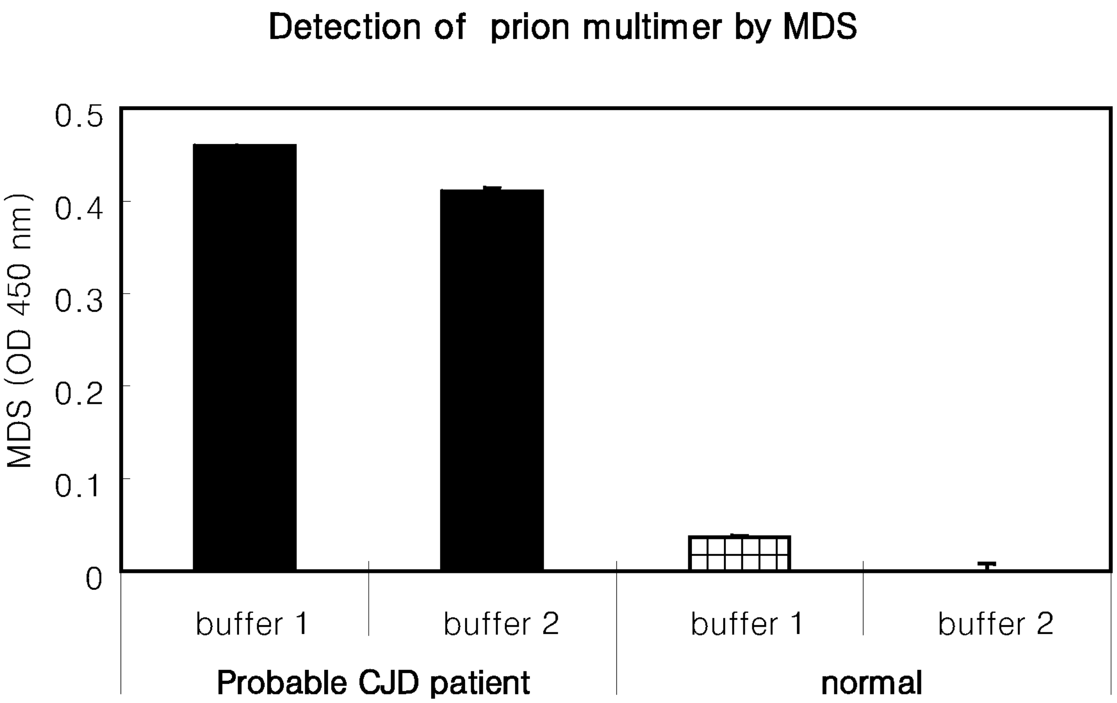
FIG. 10*b* shows the analytical results of the present process for detecting the multimeric form ($PrP^{Sc}$) of prion in plasma samples from normal or CJD (Creutzfeldt-Jakob disease) human.

Plasmas from hamster and human did not show any signal, indicating the absence of prion multimers, as shown in FIGS. 10*a* and 10*b*. On the other hand, the signals were observed from the plasmas from scrapie hamster and human CJD patients, indicating the presence of prion multimers. It could be appreciated that the sensitivity of the MDS could go down to 5 μl of the plasma based on the results that the use of 24 μl of plasma (yielding 24%) in this Example allows for the successful detection of multimeric form of prion. In FIG. 10, buffer 1 and buffer 2 denote the different blocking buffers for processing the coated plates. Buffer 1 and 2 represent the coated plated blocked with Block Ace (25%, Serotec) and 50% Starting Block (Pierce Inc.), respectively. Not much difference was observed in using different block buffers to process the capturing antibody plates for detecting differentially the $PrP^{Sc}$ multimers from the normal $PrP^{c}$.

Example XI

Detection of $PrP^{Sc}$ Using Cocktailed Capturing Antibody

3O8-coated plates were prepared in two different concentrations, 150 μl of 3 or 5 μg/ml. 3F4-coated plate was made with 150 μl of 3 pg/ml. 3O8/3F4 cocktail-coated plates were made with 150 μl of 3O8 at 2.5 μg/ml and 3F4 at 1.5 μg/ml, or 3O8 at 3 μg/ml and 3F4 at 1 μg/ml. All plates were blocked with 25% Block Ace (Serotec) and washed with 300 μl of PBS.

Human plasma sample (488.4 μl) was mixed with 11.4 μl of 200 μg/ml of the human recombinant PrP and 71.4 μl of 8 M Gdn-HCl, and the mixture was incubated for 15 min at ambient temperature. The samples were diluted with 228.5 μl of 12% Triton X-100, 6% Na-deoxycholate and 1% Sarkosyl in PBS, followed by additional 1485 μl of PBS. The samples were heated for 10 min at 70° C and waited for 15 min for cooling. The samples without heating step were kept at room temperature for 10 min. The pretreated samples contain 21.4% plasma with 2.28 μg PrP, 0.25 M Gdn, 1.2% Triton X-100, 0.6% Na-deoxycholate and 0.1% Sarkosyl. Afterwards, 200 μl of samples were applied to MDS and incubated for 1 hr at 37° C. After washing the unbound samples four times from the wells with TBST (Sigma), 150 μl of 3F4-Biotin (2.5 μg/ml in TBST with 10% Startingblock) were added with incubation at 37° C. for 1 hr. The plates were washed four times with 300 μl of TBST (Sigma), and 150 μl of KPL SA-HRP (2 μg/ml in TBST with 10% Startingblock) were added to each well, followed by incubation at ambient temperature for 1 hr. The plates were washed four times with 300 μl of TBST (Sigma). TMB (150 μl, Sigma) was added to the wells and the signals were developed for 30 min. 50 μl of 1 N $H_2SO_4$ was added to stop the signal development and the signal was measured at 450 nm in the plate spectrophotometer.

Figure 11:
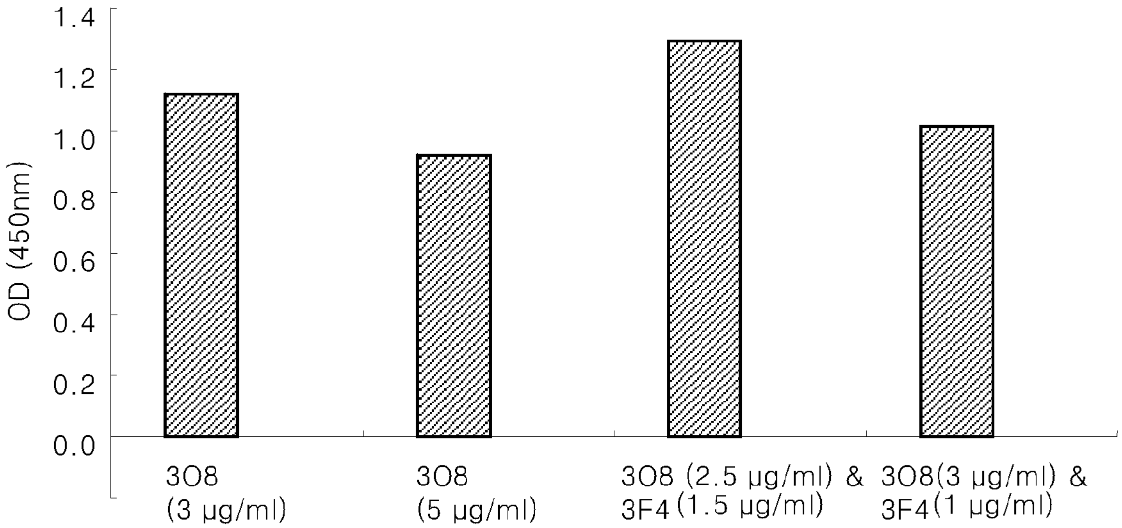
FIG. 11 shows the analytical results of the present process using cocktailed capturing antibodies for detecting the multimeric form ($PrP^{Sc}$) of prion spiked into human plasma.

The results showed not much difference in signals from 3O8-coated plates and cocktailed 3O8/3F4-coated plates, as shown in FIG. 11.

Example XII

Detection of $PrP^{Sc}$ Using Plasminogen Inhibitors

Plasminogen has been shown to bind to prion proteins, especially $PrP^{Sc}$. Plasma contains relative high concentrations of plamsinogen (300 μg/ml) in comparison with prion protein (2-20 ng/ml). Prion might exist as complex with plasminogen in plasma or other biosamples. Addition of plasmnogen in the PMCA inhibited the amplification of $PrP^{Sc}$, suggesting that plasminogen could interfere with the detection of $PrP^{Sc}$ (multimer) in plasma. Therefore, MDS was carried out with spiked human recombinant prion protein in human plasma.

3O8-coated plates were prepared in 150 μl of 5 μg/ml 3O8 antibody. Plates were blocked with 25% Block Ace (Serotec) and washed with 300 μl of PBS.

Human plasma sample (488.4 μl) was mixed with or without 11.4 μl of 200 μg/ml of the human recombinant PrP in the presence of plasminogen inhibitors, aminocaproic acid or (trans-(aminomethyl)cyclohexanecarboxylic acid, at 0, 1, 10 and 100 mM, and 71.4 μl of 8 M Gdn-HCl, and the mixture was incubated for 15 min at ambient temperature. The samples were diluted with 228.5 μl of 12% Triton X-100, 6% Na-deoxycholate and 1% Sarkosyl in PBS, followed by further addition of 1485 μl of PBS. The samples were heated for 10 min at 70° C. and waited for 15 min for cooling. The samples without heating step were kept at room temperature for 10 min. The pretreated samples contain 21.4% plasma with 2.28 μg PrP, 0.25 M Gdn, 1.2% Triton X-100, 0.6% Na-deoxycholate and 0.1% Sarkosyl. Afterwards, 200 μl of samples were applied to MDS and incubated for 1 hr at 37° C. After washing the unbound samples four times from the wells with TBST (Sigma), 150 μl of 3F4-Biotin (2.5 μg/ml in TBST with 10% Startingblock) were added with incubation at 37° C. for 1 hr. The plates were washed four times with 300 μl of TBST (Sigma), and 150 μl of KPL SA-HRP (2 μg/ml in TBST with 10% Startingblock) were added to each well, followed by incubation at ambient temperature for 1 hr. The plates were washed four times with 300 μl of TBST (Sigma). TMB (150 μl, Sigma) was added to the wells and the signals were developed for 30 min. 50 μl of 1 N $H_2SO_4$ was added to stop the signal development and the signal was measured at 450 nm in the plate spectrophotometer.

The experiments show the analytical results of the present process using plasminogen inhibitors, amino caproic acid (ACA) or trans-(aminomethyl)cyclohexanecarboxylic acid acid (AMCHA), for enhancing the detection of the multimeric form ($PrP^{Sc}$) of human recombinant prion protein spiked into human plasma (see Table 2). Values in Table 2 are optical density at 450 nm. ACA and AMCHA at all concentrations in the sample preparation buffer enhanced the detection of spiked human recombinant prion protein in human plasma. Plamsminogen inhibitors, ACA, AMCHA, or other will enhance the detection of $PrP^{Sc}$ (multimers) in biosamples, by displacing the plasminogen from $PrP^{Sc}$ in the sample.

TABLE 2

| Inhibitor to plasminogen | Plasma with human recombinant PrP | Only Plasma | Non-specific binding | Ratio of Signals** |
|---|---|---|---|---|
| AMCHA 100 mM | 0.751* | 0.4339* | 0.4933* | 1.7 |
| AMCHA 10 mM | 0.7155 | 0.453 | 0.4753 | 1.6 |
| AMCHA 1 mM | 0.711 | 0.3855 | 0.4499 | 1.8 |
| ACA 100 mM | 0.52 | 0.4036 | 0.4665 | 1.3 |
| ACA 10 mM | 0.5723 | 0.4098 | 0.4128 | 1.4 |
| ACA 1 mM | 0.6507 | 0.3737 | 0.4549 | 1.7 |
| No treatment | 1.1961 | 1.1702 | 0.5325 | 1.0 |

*optical density at 450 nm

**ratio of signals from spiked plasma and only plasma samples

Example XIII

Detection of $PrP^{Sc}$ from Mouse Brain Spiked into Bovine Plasma Using Other Antibody Set The purified $PrP^{Sc}$ from scrapie mouse brain was spiked into 100% bovine plasma and applied to the MDS by following the above MDS protocol as described in Example VIII. Briefly, 0.0083, 0.0028, 0.0009, 0.0003 and 0% purified $PrP^{Sc}$ were diluted into 100% bovine plasma, yielding approximately 0.0033, 0.0011, 0.0004, 0.0001 and 0 μg/ml. 100 μl of the spiked plasmas were incubated onto 4E10-coated plates for 1 hr at 37° C. 4E10 antibody was gift from National Institute of Animal Health (Japan). After washing the plate four times with TBST, the 4E10-HRP detection antibody was added, followed by 1 hr incubation at ambient temperature. The plate was washed four times with TBST and chemiluminascent substrate (Femto, Pierce) was added. The plate was read at the chemiluminometer.

Figure 12:
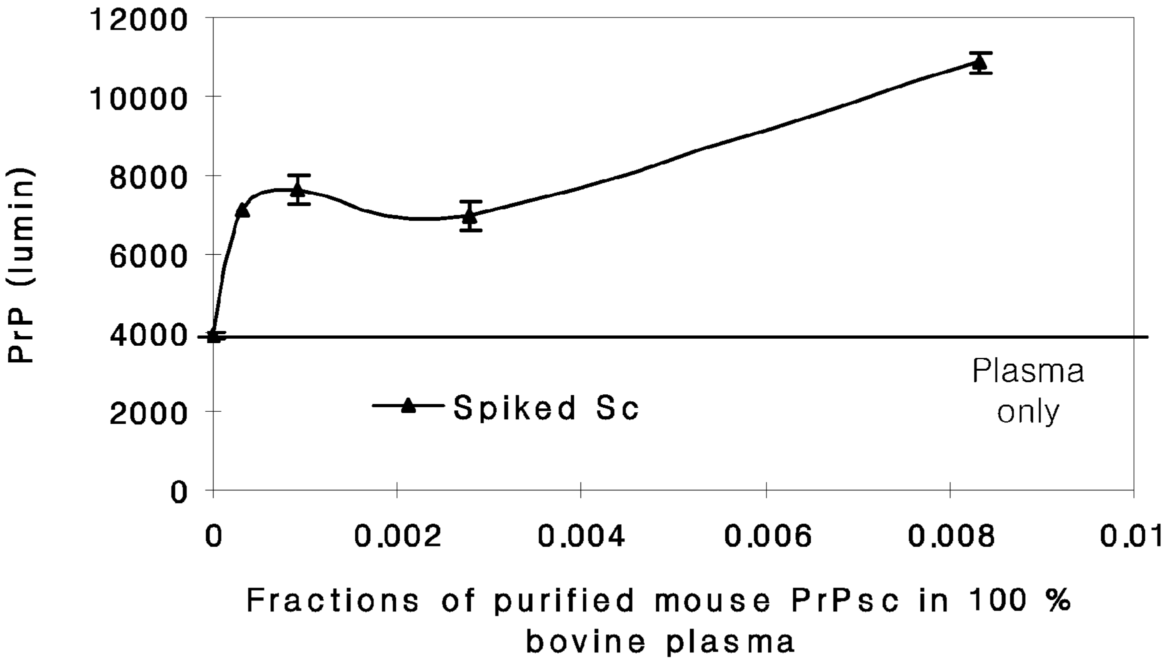
FIG. 12 is a graph showing the results of the present method for detecting the multimeric form ($PrP^{Sc}$) of prion spiked into bovine plasma.

The results show that purified $PrP^{Sc}$ (multimeric form of prion) from scrapie mouse brain in 100% bovine plasma was detected by MDS in a concentration-dependent manner, as shown in FIG. 12. Bovine plasma sample without purified $PrP^{Sc}$ from scrapie mouse brain did not show any signal. In addition, 4E10 antibody against amino acid 187-197 of prion could be used in MDS, supporting that the MDS is not sequence and region specific system.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for differentially detecting a multimeric form from a monomeric form of a multimer-forming polypeptide in a biosample, comprising:

(a) contacting the biosample to a capturing antibody recognizing an epitope on the multimer-forming polypeptide to capture the monomeric form, multimeric form or monomeric and multimeric forms;

(b) contacting the monomeric form, multimeric form or monomeric and multimeric forms captured by the capturing antibody to a detecting antibody recognizing an epitope which is overlapped with, but not identical to the epitope of (a); wherein said detecting antibody is linked to a label generating a detectable signal; and said epitope recognized by the capturing antibody or detecting antibody is not repeated in the monomeric form of a multimer-forming polypeptide; and (c) detecting the formation of a multimeric form-detection antibody complex by measuring a signal generated from the label linked to the detecting antibody.

2. The method according to claim 1, wherein said multimer-forming polypeptide is selected from the group consisting of Aβ peptide, β-amyloid, tau protein, prion, α-synuclein, Ig light chains, serum amyloid A, transthyretin, cystatin C, $\beta_2$-microglobulin, huntingtin, superoxide dismutase, serpin and amylin.

3. The method according to claim 2, wherein said multimer-forming polypeptide is prion.

4. The method according to claim 3, wherein said monomeric form is $PrP^c$ and said multimeric form is $PrP^{Sc}$.

5. The method according to claim 1, wherein said capturing antibody is bound to a solid substrate.

6. The method according to claim 1, wherein said label linked to the detecting antibody is selected from the group consisting of a chemical, an enzymatic, a radioactive, a fluorescent, a luminescent, a chemiluminescent and a FRET label.

7. The method according to claim 1, wherein said biosample is a brain homogenate or plasma.

8. The method according to claim 7, further comprising treating the biosample with trypsin prior to the contacting of (a) when the brain homogenate is used as the biosample.

9. The method according to claim 1, further comprising treating the biosample with a protein denaturing agent prior to the contacting of (a).

10. The method according to claim 1, further comprising heating the biosample prior to the contacting of (a).

11. The method according to claim 7, wherein said biosample comprises sarkosyl detergent when the plasma is used as the biosample.

12. The method according to claim 7, wherein the method comprises no protease treatment step when the plasma is used as the biosample.

13. The method according to claim 7, further comprising treating the biosample with an inhibitor to plasminogen prior to the contacting of (a) when the plasma is used as the biosample.

14. The method according to claim 13, wherein said inhibitor to plasminogen is selected from the group consisting of omega-aminocarboxylic acids, L-lysine and its derivatives, zwitterions, benzylamine, benzamidine, L-arginine and its derivatives.

15. The method according to claim 1, wherein said capturing and/or detecting antibody recognizes an epitope having an amino acid sequence spanning amino acid 109-112, 106-126, 132-147 or 135-140 of SEQ ID NO:1 when described by a human prion sequence.

16. The method according to claim 15, wherein said bio-sample is a bovine brain homogenate and said capturing and/or detecting antibody recognizes an epitope having an amino acid sequence spanning amino acid 145-150 or 142-157 of SEQ ID NO: 2 when described by a bovine prion sequence.

17. The method according to claim 15, wherein said bio-sample is a human plasma and said capturing and/or detecting antibody recognizes an epitope having an amino acid sequence spanning amino acid 109-112 or 106-126 of SEQ ID NO:1 when described by a human prion sequence.

* * * * *

SEQUENCE LISTING

<160> NUMBER OF SEQ ID NOS: 2

<210> SEQ ID NO 1
<211> LENGTH: 253
<212> TYPE: PRT
<213> ORGANISM: human

<400> SEQUENCE: 1

Met Ala Asn Leu Gly Cys Trp Met Leu Val Leu Phe Val Ala Thr Trp
1 5 10 15

Ser Asp Leu Gly Leu Cys Lys Lys Arg Pro Lys Pro Gly Gly Trp Asn
20 25 30

Thr Gly Gly Ser Arg Tyr Pro Gly Gln Gly Ser Pro Gly Gly Asn Arg
35 40 45

Tyr Pro Pro Gln Gly Gly Gly Gly Trp Gly Gln Pro His Gly Gly Gly
50 55 60

Trp Gly Gln Pro His Gly Gly Gly Trp Gly Gln Pro His Gly Gly Gly
65 70 75 80

Trp Gly Gln Pro His Gly Gly Gly Trp Gly Gln Gly Gly Gly Thr His
85 90 95

Ser Gln Trp Asn Lys Pro Ser Lys Pro Lys Thr Asn Met Lys His Met
100 105 110

Ala Gly Ala Ala Ala Ala Gly Ala Val Val Gly Gly Leu Gly Gly Tyr
115 120 125

Met Leu Gly Ser Ala Met Ser Arg Pro Ile Ile His Phe Gly Ser Asp
130 135 140

Tyr Glu Asp Arg Tyr Tyr Arg Glu Asn Met His Arg Tyr Pro Asn Gln
145 150 155 160

Val Tyr Tyr Arg Pro Met Asp Glu Tyr Ser Asn Gln Asn Asn Phe Val
165 170 175

His Asp Cys Val Asn Ile Thr Ile Lys Gln His Thr Val Thr Thr Thr
180 185 190

Thr Lys Gly Glu Asn Phe Thr Glu Thr Asp Val Lys Met Met Glu Arg
195 200 205

Val Val Glu Gln Met Cys Ile Thr Gln Tyr Glu Arg Glu Ser Gln Ala
210 215 220

Tyr Tyr Gln Arg Gly Ser Ser Met Val Leu Phe Ser Ser Pro Pro Val
225 230 235 240

Ile Leu Leu Ile Ser Phe Leu Ile Phe Leu Ile Val Gly
245 250

<210> SEQ ID NO 2
<211> LENGTH: 263
<212> TYPE: PRT
<213> ORGANISM: bovine

<400> SEQUENCE: 2

Met Val Lys Ser His Ile Gly Ser Trp Ile Leu Val Leu Phe Val Ala
1 5 10 15

Met Trp Ser Asp Val Gly Leu Cys Lys Lys Arg Pro Lys Pro Gly Gly
20 25 30

Trp Asn Thr Gly Gly Ser Arg Tyr Pro Gly Gln Gly Ser Pro Gly Gly
35 40 45

Asn Arg Tyr Pro Pro Gln Gly Gly Gly Gly Trp Gly Gln Pro His Gly
50 55 60

-continued

```
Gly Gly Trp Gly Gln Pro His Gly Gly Gly Trp Gly Gln Pro His Gly
 65                 70                  75                  80

Gly Gly Trp Gly Gln Pro His Gly Gly Gly Trp Gly Gln Pro His Gly
                85                  90                  95

Gly Gly Gly Trp Gly Gln Gly Gly Thr His Gly Gln Trp Asn Lys Pro
            100                 105                 110

Ser Lys Pro Lys Thr Asn Met Lys His Val Ala Gly Ala Ala Ala Ala
        115                 120                 125

Gly Ala Val Val Gly Gly Leu Gly Gly Tyr Met Leu Gly Ser Ala Met
    130                 135                 140

Ser Arg Pro Leu Ile His Phe Gly Ser Asp Tyr Glu Asp Arg Tyr Tyr
145                 150                 155                 160

Arg Glu Asn Met His Arg Tyr Pro Asn Gln Val Tyr Tyr Arg Pro Val
                165                 170                 175

Asp Gln Tyr Ser Asn Gln Asn Asn Phe Val His Asp Cys Val Asn Ile
            180                 185                 190

Thr Val Lys Glu His Thr Val Thr Thr Thr Thr Lys Gly Glu Asn Phe
        195                 200                 205

Thr Glu Thr Asp Ile Lys Met Met Glu Arg Val Val Glu Gln Met Cys
    210                 215                 220

Val Thr Gln Tyr Gln Lys Glu Ser Gln Ala Tyr Tyr Asp Gln Gly Ala
225                 230                 235                 240

Ser Val Ile Leu Phe Ser Ser Pro Pro Val Ile Leu Leu Ile Ser Phe
                245                 250                 255

Leu Ile Phe Leu Ile Val Gly
            260
```